(12) United States Patent
Galley et al.

(10) Patent No.: US 8,399,463 B2
(45) Date of Patent: Mar. 19, 2013

(54) IMIDAZOLE DERIVATIVES

(75) Inventors: Guido Galley, Rheinfelden (DE);
Katrin Groebke Zbinden, Liestal (CH);
Roger Norcross, Olsberg (CH); Henri Stalder, Basel (CH)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 13/235,542

(22) Filed: Sep. 19, 2011

(65) Prior Publication Data

US 2012/0004230 A1 Jan. 5, 2012

Related U.S. Application Data

(63) Continuation of application No. 12/765,898, filed on Apr. 23, 2010, now abandoned, and a continuation of application No. 11/950,449, filed on Dec. 5, 2007, now abandoned.

(30) Foreign Application Priority Data

Dec. 18, 2006 (EP) .................................... 06126307

(51) Int. Cl.
*A61K 31/5377* (2006.01)
*A61K 31/4174* (2006.01)
*A61K 31/4164* (2006.01)
*C07D 413/10* (2006.01)
*C07D 233/64* (2006.01)
*C07D 233/88* (2006.01)
*C07D 233/58* (2006.01)

(52) U.S. Cl. ...................... 514/235.8; 514/396; 514/400; 514/398; 544/139; 548/346.1; 548/341.1; 548/326.5

(58) Field of Classification Search ................ 514/235.8, 514/396, 400, 397, 398; 548/346.1, 341.1, 548/311.4, 342.1, 326.5; 544/139
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Elbe | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,125,620 A | 11/1978 | Stahle et al. | |
| 4,146,647 A | 3/1979 | Lafon | |
| 4,323,570 A | 4/1982 | Stenzel et al. | |
| 4,639,464 A | 1/1987 | Karjalainen et al. | |
| 4,665,095 A | 5/1987 | Winn et al. | |
| 4,684,659 A | 8/1987 | Karjalainen et al. | |
| 5,173,502 A | 12/1992 | Malen et al. | |
| 5,610,174 A | 3/1997 | Craig et al. | |
| 5,658,938 A | 8/1997 | Geerts et al. | |
| 2002/0019390 A1 | 2/2002 | Wong et al. | |
| 2003/0036274 A1 | 2/2003 | Boyd et al. | |
| 2003/0181354 A1 | 9/2003 | Abdulrazik | |

FOREIGN PATENT DOCUMENTS

| | | |
|---|---|---|
| CA | 2246027 | 2/2000 |
| EP | 0024829 | 3/1981 |
| EP | 0034474 | 8/1981 |
| EP | 0072615 | 2/1982 |
| EP | 0125410 | 11/1984 |
| EP | 0165779 | 12/1985 |
| EP | 0166937 | 1/1986 |
| EP | 0194984 | 9/1986 |
| EP | 0331374 | 9/1989 |
| EP | 0424059 | 4/1991 |
| EP | 0857483 | 8/1998 |
| EP | 0924209 | 6/1999 |
| EP | 1013243 | 5/2001 |
| EP | 1413576 | 4/2004 |
| EP | 0486385 | 6/2010 |
| ES | 323985 | 12/1966 |
| FR | 6551 | 12/1968 |
| GB | 725514 | 3/1955 |
| GB | 877306 | 9/1961 |
| GB | 1016514 | 1/1966 |
| JP | 49134834 | 12/1974 |
| JP | 62265270 | 11/1987 |
| JP | 63141969 | 6/1988 |
| KR | 2002/0084091 | 11/2011 |
| WO | 95/14007 | 5/1995 |
| WO | 96/22768 | 8/1996 |
| WO | 97/12874 | 4/1997 |
| WO | 98/12183 | 3/1998 |

(Continued)

OTHER PUBLICATIONS (Australian Office Action in Corres Australian Appl 2007336351 Mar. 23, 2012).
Wilkinson et al., Biochemical Pharmacology 21:3187-3192 (1972).
(Tranlsation of Jap Off Action in Corres Jap Appl 2009541972 Jul. 3, 2012).

(Continued)

*Primary Examiner* — Kristin Bianchi
(74) *Attorney, Agent, or Firm* — George W. Johnston; Patricia S. Rocha-Tramaloni; Gene J. Yao

(57) ABSTRACT

The invention relates to imidazole derivatives which have a good affinity to the trace amine associated receptors (TAARs), especially for TAAR1.
The invention also relates to a pharmaceutically-suitable acid-addition salt of the above compound.
The invention further relates to a composition comprising an imidazole derivative as described above, or a pharmaceutically-suitable acid-addition salt thereof, and to processes for preparing such compounds.

5 Claims, No Drawings

FOREIGN PATENT DOCUMENTS

| | | |
|---|---|---|
| WO | 01/30762 | 5/2001 |
| WO | 01/51472 | 7/2001 |
| WO | 01/81334 | 11/2001 |
| WO | 02/22801 | 3/2002 |
| WO | 02/40453 | 5/2002 |
| WO | 02/076950 | 10/2002 |
| WO | 03/092374 | 11/2003 |
| WO | 2004/014898 | 2/2004 |
| WO | 2006/119411 | 11/2006 |
| WO | 2007/024944 | 3/2007 |
| WO | 2008/058867 | 1/2008 |
| WO | 2008/052907 | 5/2008 |
| WO | 2008/071574 | 6/2008 |

OTHER PUBLICATIONS

Swett et al., Journal of Medical Chemistry 13(5):968-970 ( 1970).
Lindemann et al., "Trends in Pharmacol. Sci." 26:274-281 ( 2005).
Hodson et al., "Bioorgan. & Med. Chem. Letters" 12(1):3449-3452 ( 2002).
Kitbunnadaj et al., "Bioorganic & Med. Chem." 13(23):6309-6323 ( 2005).
USDIN et al., "Psychopharmacology Series" (Trace Amines and the Brain), 1:1-281 ( 1976).
Magdolen et al., "Helvetica Chimica Acta" 88:2454-2469 ( 2005).
McLennan, P. L., "European Journal of Pharmacology" 69:477-482 ( 1981).
Carroll et al., "Med. Chem. Res." 13:134-148 ( 2004).
De Bernardis et al., "J. Med. Chem." 29:1414-1417 ( 1986).
Zhang et al., "J. Med. Chem." 40:3014-3024 ( 1997).
Altenbach et al., "J. Med. Chem." 47:3220-3235 ( 2004).
Kelley et al., "CAPLUS 1981:202457".
Patani et al., "Chem. Rev." 96:3147-3176 ( 1996).
Matsunaga et al., "Bioorganic & Medicinal Chemistry":4314 ( 2004).
Bagley et al., "Medicinal Chemistry Research" 4:346-364 ( 1994).
Olmos et al., "European Journal of Pharmacology" 262:41-48 ( 1994).
Lee et al., "Bull. Korean Chem. Soc." 25:619-628 ( 2005).
Hammock et al., "Pesticide Biochem. & Physiology" 9:39-47 ( 1978).
McCormack et al., "J. Neurosci." 6:94-101 ( 1986).
Mosseau et al., "Prog. Brain res." 106:285-291 ( 1995).
Bagley et al., "Med. Chem. Res." 4(5):346-364 ( 1994).
Matsunaga et al., "Tetrahedron Asymmetry" 15:2021-2028 ( 2004).
Hart et al., "Australian J. of Chem." 24:857-864 ( 1971).
Faust et al., "J. Org. Chem." 26:4044-4047 ( 1961).
Puurunen et al., "Archives Internationales de Pharmacodynamie" 261(1):102-108 ( 1983).
Turner et al., "J. Org. Chem." 56:5739-5740 ( 1991).
Timmermans et al., "J. Med. Chem." 24:502-507 ( 1981).
Wainscott et al., "J. of Pharmacology & Exp. Therapeutics" 320:475-485 ( 2007).
Hirashima et al., "Bioorganic & Medicinal Chemistry" 10:117-123 ( 2002).
Wentland et al., "J. Med. Chem." 30:1482-1489 ( 1987).
"Translation of Chinese Office Action 200780046997.2" , 2007.
CAPLUS, "20361" ( 1956).
Law et al., "J. Med. Chem." 41:2243-2251 ( 1998).
Ruskoaho et al., "Arch. Pharmacol." 322:279-285 ( 1983).
Lindemann et al., "Genomics" 85:372-385 ( 2005).
Nathanson, J. A., "Amer. Soc. Pharmacology" 28:254-268 ( 1985).
Ojida et al., "Tetrahedron Asymmetry" 15:1555-1559 ( 2004).
Jetter et al., "Synthesis":829-831 ( 1998).
Bunzow et al., "Molecular Pharmacology" 60:1181-1188 ( 2001).
Branchek et al., "Curr. Opin. Pharmacol." 3:90-97 ( 2003).
Timmermans et al., "Life Sciences" 28:653-660 ( 1981).
Amemiya et al., "J. Med. Chem." 35:750-755 ( 1992).
"Office Action corresponding to Chilean Patent Application 3653-2007 and Cover Letter dated Jan. 6, 2011".
Prisinzano et al., "Bioorganic & Medicinal Chemistry Letter" 14:4697-4699 ( 2004).
Amick et al., "Tetrahedron Letters" 27:901-904 ( 1986).
Cordi et al., "J. Med. Chem." (XP002283814), 25(7):557-568 ( 1990).
Ruoff et al., "J. Amer. Chem. Soc." 72:4950-4953 ( 1950).
De Bernardis et al., "J. Med. Chem." 30:1011-1017 ( 1987).
Zucchi et al., "Brit. J. of Pharmacology" (XP002473114), 149:967-978 ( 2006).
Savola et al., "Drug Res." 38:29-35 ( 1988).
Holt, A., "Journal of Psychiatry & Neuroscience" 28:409-414 ( 2003).
(Registry No. 700355-78-8 Jun. 28, 2004).
Searched in Caplus (Registry No. 401-45-6 Nov. 16, 1984).
(Translation of Chinese Off Act in Corres Chinese Appl 2007800469972 Sep. 18, 2012).
(Registry No. 802322-21-0 Dec. 25, 2004).

IMIDAZOLE DERIVATIVES

PRIORITY TO RELATED APPLICATION(S)

This application is a continuation of U.S. application Ser. No. 12/765,898, filed Apr. 23, 2010, now pending; which is a continuation of U.S. application Ser. No. 11/950,449, filed Dec. 5, 2007, now abandoned; which claims the benefit of European Patent Application No. 06126307.5, filed Dec. 18, 2006. The entire contents of the above-identified applications are hereby incorporated by reference.

FIELD OF THE INVENTION

This invention relates to compounds which have a good affinity to the trace amine associated receptors (TAARs), especially for TAAR1.

These compounds are useful in the treatment or prevention of, inter alia, disorders of the central nervous system, for example, the treatment or prevention of depression, psychosis, Parkinson's disease, anxiety and/or attention deficit hyperactivity disorder (ADHD).

The invention relates also to processes for preparing such compounds and a pharmaceutical composition comprising such a compound.

BACKGROUND OF THE INVENTION

The classical biogenic amines (serotonin, norepinephrine, epinephrine, dopamine, histamine) play important roles as neurotransmitters in the central and peripheral nervous system. Deutch, A. Y. and Roth R. H. (1990) Neurotransmitters. In *Fundamental Neuroscience* (2nd ed.) (Zigmond, M. J., Bloom, F. E., Landis, S. C., Roberts, J. L., and Squire L. R., eds.) 193-234, Academic Press. Their synthesis and storage, as well as their degradation and reuptake after release are tightly regulated. An imbalance in the levels of biogenic amines is known to be responsible for the altered brain function under many pathological conditions. Wong, M. L. and Licinio, J. (2001) *Nat. Rev. Neurosci.* 2, 343-351; Carlsson, A. et al. (2001), *Annu. Rev. Pharmacol. Toxicol.* 41, 237-260; Tuite, P. and Riss, J. (2003), *Expert Opin. Investig. Drugs* 12, 1335-1352; Castellanos, F. X. and Tannock, R. (2002), *Nat. Rev. Neurosci.* 3, 617-628.

A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines. Usdin, E. and Sandler, M. eds. (1984), *Trace Amines and the brain*, Dekker. Their disregulation has been linked to various psychiatric diseases like schizophrenia and depression and for other conditions like attention deficit hyperactivity disorder, migraine headache, Parkinson's disease, substance abuse and eating disorders. Lindemann, L. and Hoener, M. (2005), *Trends in Pharmacol. Sci.* 26, 274-281; Branchek, T. A. and Blackburn, T. P. (2003), *Curr. Opin. Pharmacol.* 3, 90-97; Premont, R. T. et al. (2001), *Proc. Natl. Acad. Sci. U.S.A.* 98, 9474-9475.

For a long time, TA-specific receptors had only been hypothesized based on anatomically discrete high-affinity TA binding sites in the central nervous system of humans and other mammals. Mousseau, D. D. and Butterworth, R. F. (1995), *Prog. Brain Res.* 106, 285-291; McCormack, J. K. et al. (1986), *J. Neurosci.* 6, 94-101. Accordingly, the pharmacological effects of TAs were believed to be mediated through the well known machinery of classical biogenic amines, by either triggering their release, inhibiting their reuptake or by "crossreacting" with their receptor systems. Premont, R. T. et al. (2001), *Proc. Natl. Acad. Sci. U.S.A.* 98, 9474-9475; Dyck, L. E. (1989), *Life Sci.* 44, 1149-1156; Parker, E. M. and Cubeddu, L. X. (1988), *J. Pharmacol. Exp. Ther.* 245, 199-210. This view changed significantly with the recent identification of several members of a novel family of GPCRs, the trace amine associated receptors (TAARs). Lindemann, L. and Hoener, M. (2005), *Trends in Pharmacol. Sci.* 26, 274-281; Lindemann, L. et al. (2005), *Genomics* 85, 372-385.

There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies. Lindemann, L. and Hoener, M. (2005), *Trends in Pharmacol. Sci.* 26, 274-281; Lindemann, L. et al. (2005), *Genomics* 85, 372-385. TAAR1 is in the first subclass of four genes (TAAR1-4) highly conserved between human and rodents. TAs activate TAAR1 via Gαs. Disregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

It has been found that the compounds of formula I (described below) have a good affinity to the TAARs, especially for TAAR1.

The compounds as useful in the treatment or prevention of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and/or cardiovascular disorders. Preferably, the compounds are useful in the treatment or prevention of disorders of the central nervous system, for example, the treatment or prevention of depression, psychosis, Parkinson's disease, anxiety and/or attention deficit hyperactivity disorder (ADHD).

SUMMARY OF THE INVENTION

The present invention is directed to a compound according to formula I,

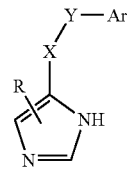

I wherein
R is selected from the group consisting of hydrogen, lower alkyl and amino;
X is selected from the group consisting of —CH₂—, —CH(lower alkoxy)-, —CH(OH)—, and —NH—;
Y is selected from the group consisting of —CH₂, —CH(lower alkyl)-, —CH(lower alkoxy)-, —O—, —S—, —S(O)—, —S(O)₂—, —CH(phenyl)- and —C(lower alkyl)₂-; and
Ar is selected from the group consisting of phenyl, napthtyl and benzofuranyl, said phenyl, mapthyl, or benzofuranyl being unsubstituted or substituted by one or more substituents, each substituent being independently selected from the group consisting of lower alkyl, lower alkyl substituted by halogen, halogen, lower alkoxy, lower alkoxy substituted by halogen, hydroxy, amino, di-alkylamino, morpholinyl, phenyl, benzyl and O-benzyl;
with the provisio that, wherein, when X is —NH—, Y is selected from the group consisting of —CH₂, —CH(lower alkyl)-, —CH(lower alkoxy)-, —CH(phenyl)- or —C(lower alkyl)₂-; and
the further proviso that said compound is not
5-phenethyl-1H-imidazole,
5-(2-phenyl-propyl)-1H-imidazole,
1-(1H-imidazol-4-yl)-2-phenyl-ethanol,
5-(2,2-diphenyl-ethyl)-1H-imidazole,
4-(2-m-tolyl-ethyl)-1H-imidazole,
4-[2-(2,6-dimethyl-phenyl)-ethyl]-1H-imidazole,
4-(biphenyl-2-yloxymethyl)-1H-imidazole,
5-(2-methyl-2-phenyl-propyl)-1H-imidazole,
4-(2-chloro-phenoxymethyl)-1H-imidazole,
4-(2-fluoro-phenoxymethyl)-1H-imidazole,
4-o-tolyloxymethyl-1H-imidazole,
4-(3-chloro-phenoxymethyl)-1H-imidazole,
4-(2,6-dimethyl-phenoxymethyl)-1H-imidazole, or
5-methyl-4-phenylsulfanylmethyl-1H-imidazole.

The present invention also relates to a pharmaceutically-suitable acid-addition salt of such a compound.

The invention includes all racemic mixtures, all their corresponding enantiomers and/or optical isomers.

In addition, all tautomeric forms of compounds of formula I are also encompassed by the present invention.

The present invention is also directed to processes for the preparation of the above compound.

The present invention is also directed to a pharmaceutical composition comprising the above compound or a pharmaceutically-suitable acid-addition salt thereof.

Compounds according to the present invention have a good affinity to the TAARs, especially for TAAR1. Such compounds are useful in the treatment or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders. Preferably, the compounds of the present invention are useful in the treatment or prevention of disorders of the central nervous system, for example, the treatment or prevention of depression, psychosis, Parkinson's disease, anxiety and/or attention deficit hyperactivity disorder (ADHD).

DETAILED DESCRIPTION OF THE INVENTION

The present invention is directed to a compound according to formula I,

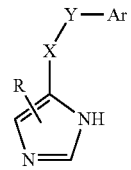

wherein
R is selected from the group consisting of hydrogen, lower alkyl and amino;
X is selected from the group consisting of —CH₂—, —CH(lower alkoxy)-, —CH(OH)—, and —NH—;
Y is selected from the group consisting of —CH₂, —CH(lower alkyl)-, —CH(lower alkoxy)-, —O—, —S—, —S(O)—, —S(O)₂—, —CH(phenyl)- and —C(lower alkyl)₂-; and
Ar is selected from the group consisting of phenyl, napthtyl and benzofuranyl, said phenyl, mapthyl, or benzofuranyl being unsubstituted or substituted by one or more substituents, each substituent being independently selected from the group consisting of lower alkyl, lower alkyl substituted by halogen, halogen, lower alkoxy, lower alkoxy substituted by halogen, hydroxy, amino, di-alkylamino, morpholinyl, phenyl, benzyl and O-benzyl;
with the provisio that, wherein, when X is —NH—, Y is selected from the group consisting of —CH₂, —CH(lower alkyl)-, —CH(lower alkoxy)-, —CH(phenyl)- or —C(lower alkyl)₂-; and
the further proviso that said compound is not
5-phenethyl-1H-imidazole,
5-(2-phenyl-propyl)-1H-imidazole,
1-(1H-imidazol-4-yl)-2-phenyl-ethanol,
5-(2,2-diphenyl-ethyl)-1H-imidazole,
4-(2-m-tolyl-ethyl)-1H-imidazole,
4-[2-(2,6-dimethyl-phenyl)-ethyl]-1H-imidazole,
4-(biphenyl-2-yloxymethyl)-1H-imidazole,
5-(2-methyl-2-phenyl-propyl)-1H-imidazole,
4-(2-chloro-phenoxymethyl)-1H-imidazole,
4-(2-fluoro-phenoxymethyl)-1H-imidazole,
4-o-tolyloxymethyl-1H-imidazole,
4-(3-chloro-phenoxymethyl)-1H-imidazole,
4-(2,6-dimethyl-phenoxymethyl)-1H-imidazole, or
5-methyl-4-phenylsulfanylmethyl-1H-imidazole.

The present invention also relates to a pharmaceutically-suitable acid-addition salt of such a compound.

The invention includes all racemic mixtures, all their corresponding enantiomers and/or optical isomers.

In addition, all tautomeric forms of compounds of formula I are also encompassed by the present invention.

The present invention is also directed to processes for the preparation of the above compound.

As used herein, the term "halogen" refers to chlorine, iodine, fluorine or bromine.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred lower alkyl groups are groups with 1 to 4 carbon atoms.

As used herein, the term "lower alkyl substituted by halogen" denotes a lower alkyl group as defined above, wherein at least one hydrogen atom is replaced by halogen, for example —CF$_3$, —CHF$_2$, —CH$_2$F, —CH$_2$CF$_3$, —CH$_2$CH$_2$CF$_3$, —CH$_2$CF$_2$CF$_3$ and the like.

As used herein, the term "lower alkoxy" denotes a substituent wherein the alkyl residue is attached to the remainder of the molecule via an oxygen group.

The term "pharmaceutically-suitable acid-addition salt" embraces salts of a compound of formula I with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like, the salt not being toxic and not interfering with the ability of the compound of formula I to elicit the biological or medical response of a tissue system, animal or human, that is being sought by the researcher, veterinarian, medical doctor or other clinician.

Preferred compounds of the present invention are those of formula I wherein X and Y are both —CH$_2$—. Such compounds include:

4-[2-(2-chloro-phenyl)-ethyl]-1H-imidazole;
4-[2-(2-methoxy-phenyl)-ethyl]-1H-imidazole;
4-[2-(3-chloro-phenyl)-ethyl]-1H-imidazole;
4-[2-(3-fluoro-phenyl)-ethyl]-1H-imidazole;
4-[2-(3-trifluoromethyl-phenyl)-ethyl]-1H-imidazole;
4-[2-(3-methoxy-phenyl)-ethyl]-1H-imidazole;
4-[2-(4-chloro-phenyl)-ethyl]-1H-imidazole;
4-[2-(3,5-dichloro-phenyl)-ethyl]-1H-imidazole; and
pharmaceutically-suitable acid-addition salts thereof.

Also preferred are compounds of the present invention are those of formula I wherein X is —CH$_2$— and Y is —CH (lower alkyl), for example the following compounds:

4-(2-phenyl-butyl)-1H-imidazole; and
pharmaceutically-suitable acid-addition salts thereof.

Additional preferred are compounds of the present invention are those of formula I wherein X is —CH$_2$— and Y is —O—, for example the following compounds:

4-(2,3-dichloro-phenoxymethyl)-1H-imidazole;
4-(2,3-difluoro-phenoxymethyl)-1H-imidazole;
4-(3,4-dichloro-phenoxymethyl)-1H-imidazole;
4-(4-chloro-3-fluoro-phenoxymethyl)-1H-imidazole;
5-(benzofuran-6-yloxymethyl)-1H-imidazole; and
pharmaceutically-suitable acid-addition salts thereof.

Yet another preferred embodiment of the present invention are compounds of formula I, wherein X is —CH$_2$— and Y is —S—, for example the following compounds:

5-(2,3-dichloro-phenylsulfanylmethyl)-1-imidazole;
4-(4-chloro-phenylsulfanylmethyl)-5-methyl-1H-imidazole;
4-(naphthalen-2-ylsulfanylmethyl)-1H-imidazole; and
pharmaceutically-suitable acid-addition salts thereof.

The present compounds of formula I and their pharmaceutically-suitable acid-addition salts can be prepared by various processes, for example, by a process comprising a) deprotecting a compound of formula

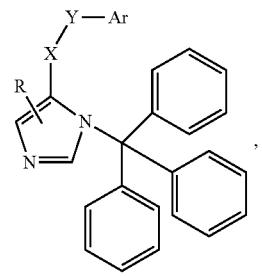

II to produce a compound of formula

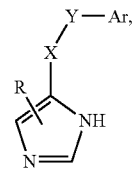

I wherein the definitions are as described above, or b) hydrogenating a compound of formula

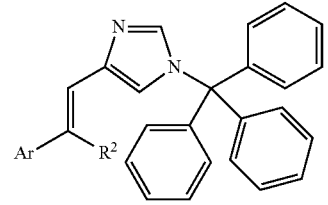

V to produce a compound of formula

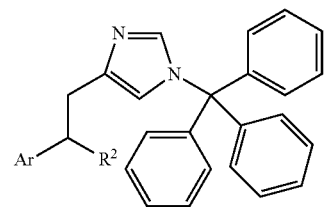

II-1 and deprotecting the compound of formula II-1 in a step analogous to step (a) to produce a compound of formula

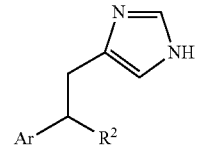

I-1 wherein Ar is as defined above and R$^2$ is hydrogen, lower alkyl or lower alkoxy, or c) alkylating a compound of formula

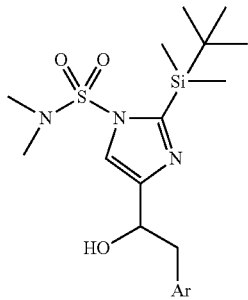

to produce a compound of formula

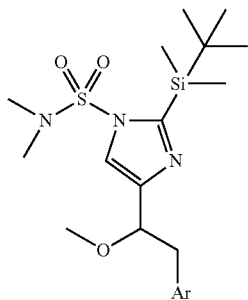

and deprotecting the compound of formula II-2 in a step analogous to step (a) to produce a compound of formula

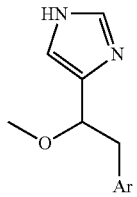

I-2 wherein Ar is as defined above; or
d) reacting a compound of formula

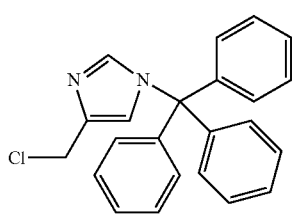

XI and a compound of formula

ArOHX to produce a compound of formula

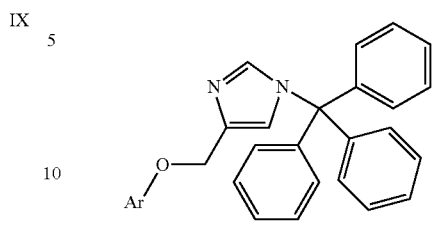

IX and deprotecting the compound of formula II-3 in a step analogous to step (a) to produce a compound of formula

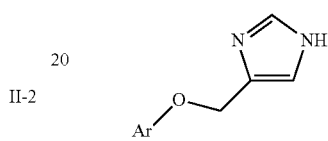

I-3 wherein the definitions are as described above, or
e) reacting a compound of formula

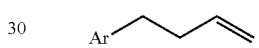

XII with acetonitrile to produce a compound of formula

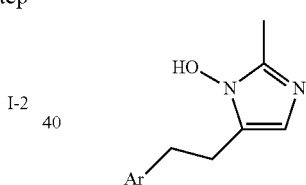

XIII and removing the hydroxy group to produce a compound of formula

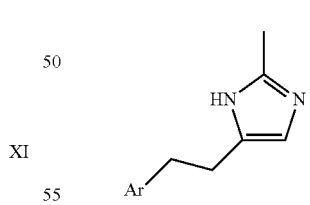

I-4 wherein Ar is as defined above, or
f) reacting a compound of formula

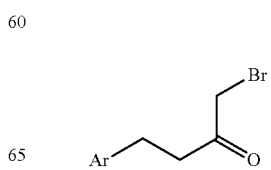

XIII with a compound of formula

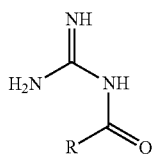

to produce a compound of formula

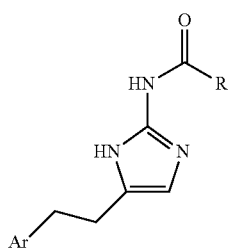

and deprotecting to produce a compound of formula

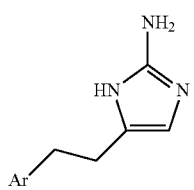

wherein R is lower alkyl and Ar is as described above, or
g) reacting a compound of formula

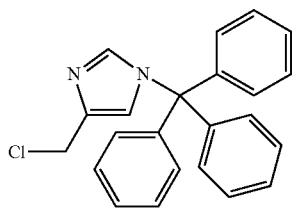

and a compound of formula

ArSHX' to produce a compound of formula

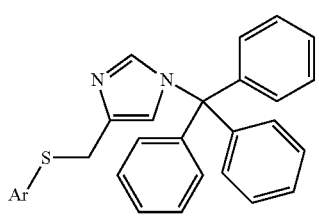

and deprotecting the compound of formula II-4 in a step analogous to step (a) to produce a compound of formula

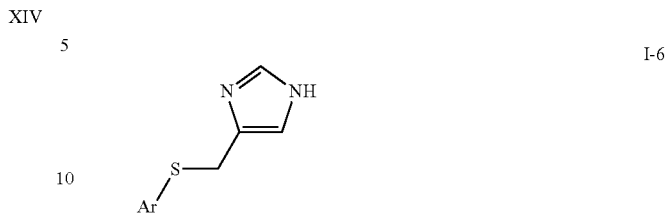

wherein Ar is as defined above, or
h) oxidizing a compound of formula

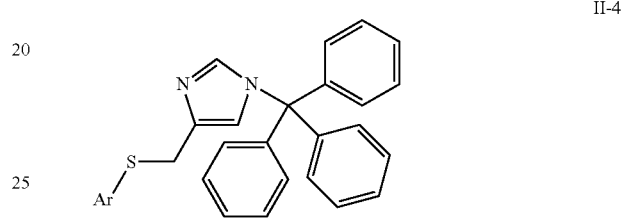

to produce a compound of formulas

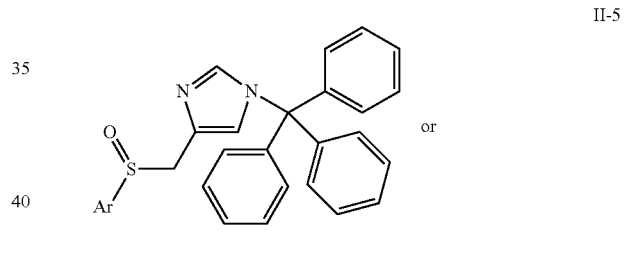

and deprotecting said compound of formula II-5 or formula II-6 in a step analogous to step (a) to produce a compound of formulas

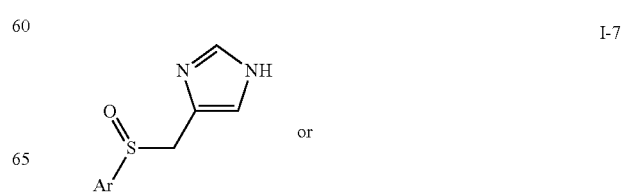

-continued

I-8

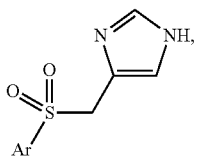

respectively, wherein Ar is as defined above; or i) reducing a compound of formula

IXX

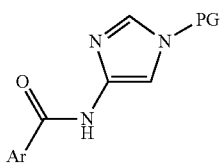

to produce a compound of formula

II-7

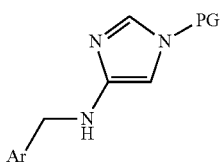

and deprotecting the compound of formula II-7 in a step analogous to step (a) to produce a compound of formula

I-9

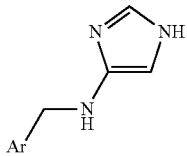

wherein Ar is as described above and PG is a common N-protecting group.

If desired, the above produced compounds of formula I may be converted into pharmaceutically-suitable acid-addition salts.

The following are general schemes which exemplify the use of the above processes in the production of compounds of formula I. The starting materials are either commercially available (e.g., from one or more of the following chemical suppliers such as Aldrich, Fluka, Acros, Maybridge, Avocado, TCI, or additional suppliers as indicated in databases such as Chemical Abstracts [American Chemical Society, Columbus, Ohio] or Available Chemicals Director [Elsevier MDL, San Ramon, Calif.]), are otherwise known in the chemical literature, or may be prepared in accordance with methods well known in the art.

Procedure A

Synthesis of C—C-Linked Compounds

Scheme 1

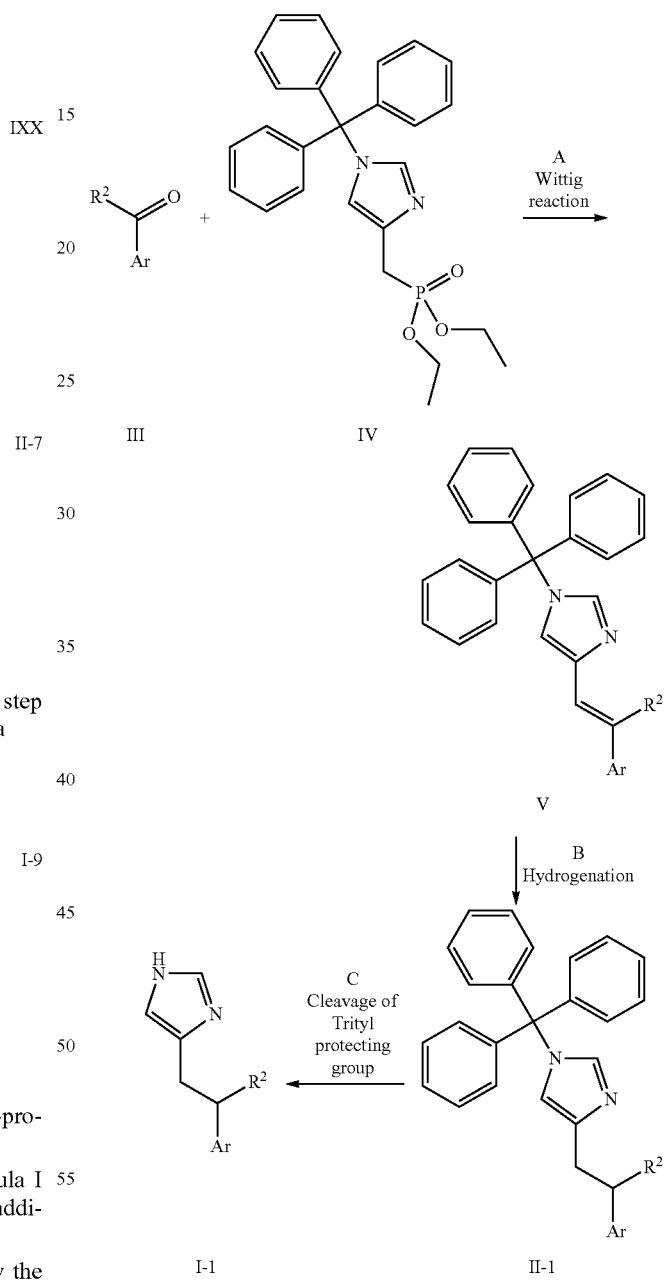

$R^2$ is lower alkyl or hydrogen.

Step A:

The Wittig reaction between an aldehyde or a ketone of formula III and (1-trityl-1H-imidazol-4-ylmethyl)-phosphonic acid diethyl ester (IV) can be accomplished by using a base such as NaH, KO-tert-butyl (KOtBu), NaOCH$_3$, NaOCH$_2$CH$_3$, n-butyllithium, LiHMDS, NaHMDS, KHMDS, and LDA in a solvent such as tetrahydrofuran (THF), dioxane, acetonitrile, 1,2-dimethoxyethan, DMF, benzene, toluene or mixtures thereof at temperatures from −78° C.-80° C. for 15 minutes-8 hours and, if appropriate, optional addition of a crown ether for ylide generation and then condensing the ylide with the carbonyl compound in the same solvent at a temperature between 0 and 80° C. for 1-24 hours. Alternatively, the base, the carbonyl compound and the optional crown ether can be added to the reaction mixture at the same time without preformation of the ylide at temperatures from −78° C.-80° C.

Preferred conditions for reactions with aryl ketones are ylide formation at room temperature using KOtBu as the base and THF as the solvent, reacting the phosphonic acid ester for 15 minutes at room temperature, and then condensation with the carbonyl component at 80° C. overnight. Preferred conditions for benzaldehydes are ylide formation in the presence of the carbonyl compound using KOtBu as the base and THF as the solvent at 80° C. overnight.

Step B:

The reduction of the alkene of formula V can be effected by hydrogenation with hydrogen under normal or elevated pressure or by transfer hydrogenation using ammonium formiate or cyclohexadiene as a hydrogen source with a catalyst such as $PtO_2$, Pd—C or Raney nickel in solvents such as methanol (MeOH), ethanol (EtOH), $H_2O$, dioxane, THF, HOAc, EtOAc, $CH_2Cl_2$, $CHCl_3$, DMF or mixtures thereof. Alternatively, the reduction of the alkene can be effected by Mg in MeOH or by $LiAlH_4$ in THF or diethylether.

The preferred procedure for trisubstituted alkenes is hydrogenation at normal pressure in MeOH/$CH_2Cl_2$ using 10% Pd/C as catalyst. The preferred procedure for disubstituted alkenes is hydrogenation at normal pressure in MeOH/$CHCl_3$/AcOH using 10% Pd/C as catalyst. Both conditions may lead to partial loss of the trityl protecting group. In this case the mixture of protected and unprotected products is subjected directly to conditions C.

Step C:

The cleavage of the trityl group can be effected with a mineral acid such as HCl, $H_2SO_4$ or $H_3PO_4$ or a organic acid such as $CF_3COOH$, $CHCl_2COOH$, HOAc or p-toluenesulfonic acid in a solvent such as $CH_2Cl_2$, $CHCl_3$, THF, MeOH, EtOH or $H_2O$ at 0 to 60° C.

Preferred conditions are 2N HCl in EtOH at reflux for 1-3 hours.

Procedure B

Synthesis of C—C-Linked Compounds with Alkoxy Substituent in a Position to Imidazoles Scheme 2

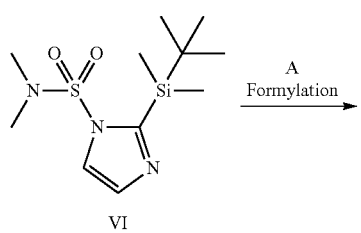

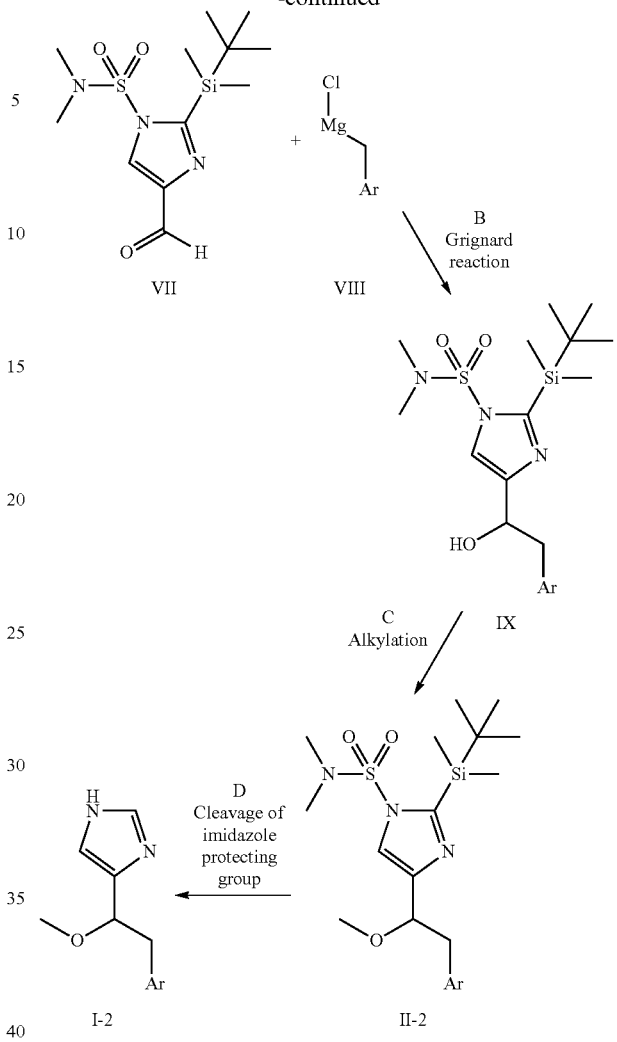

Step A:

The formylation of 2-(tert-butyl-dimethyl-silanyl)-imidazole-1-sulfonic acid dimethyl-amide (VII) can be effected by deprotonation with a strong base such as n-butyllithium, s-butyllithium or t-butyllithium and optionally an additive such as tetramethylethylene diamine or pentamethyl diethylene triamine in a solvent such as THF or diethylether at −78° C.-−40° C., followed by quenching the anion with a formylating electrophile such as DMF at −78° to room temperature for 1-24 hours.

Preferred conditions are deprotonation with n-butyllithium at −78° C. for 10 minutes, then reaction with DMF at −78° C. for 2 hours.

Step B:

The Grignard reaction of the protected formyl imidazole (VII) with an aryl magnesium chloride or bromide (VIII) can be effected by adding a solution of the Grignard reagent (commercially available or prepared form a benzyl chloride or bromide and Mg by standard methods) in a solvent such as diethylether, THF or benzene to a solution of the aldehyde in one of the previously mentioned solvents at −20° C. to room temperature and letting the two components react at room temperature to reflux temperature for 1-24 hours.

Preferred conditions involve addition of the Grignard reagent in diethylether to a solution of aldehyde in THF at room temperature and reaction at room temperature overnight.

Step C:

The alkylation of the alcohol of formula IX can be accomplished by deprotonation of the hydroxy group with a base such as NaH, KH, n-butyllithium, KOtBu, KOH or aqueous NaOH and KOH in the presence of a phase transfer catalyst (tetraalkylammonium salts) in a suitable solvent such as THF, DMF, DMSO, toluene or 1,2-dimethoxyethane at −78° C. to room temperature for 30 minutes-2 hours and subsequent addition of an alkyl halide.

Preferred conditions are deprotonation with NaH in THF at room temperature for 1 hour and alkylation with an alkyl iodide at room temperature overnight.

Step D:

The simultaneous cleavage of both protecting groups (II-2) can be achieved in the presence of a mineral acid such as HCl, HBr or $H_2SO_4$ in a solvent such as EtOH, MeOH, $H_2O$ or THF at room temperature reflux temperature for 1-24 hours.

Preferred conditions are 2N HCl in EtOH at reflux for 1-3 hours.

Procedure C

Synthesis of C—O-Linked Compounds

Scheme 3

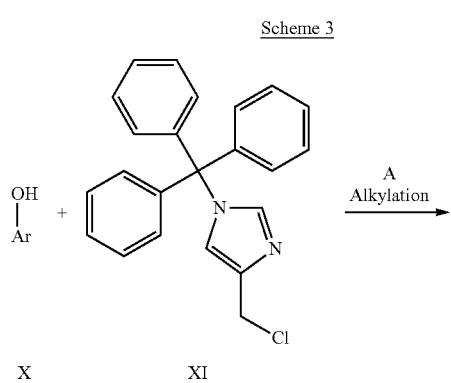

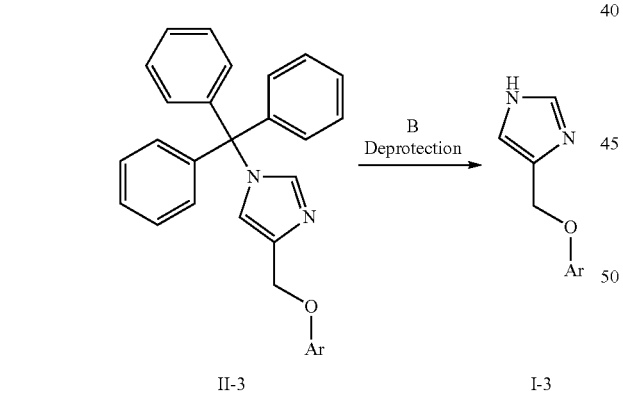

Step A:

The alkylation of a substituted phenol with 4-chloromethyl-1-trityl-1H-imidazole (XI) can be accomplished using a base such as $K_2CO_3$, $Cs_2CO_3$, $Na_2CO_3$, $NaHCO_3$, aqueous NaOH, KOH, LiOH, NaH, $NaOCH_3$, $NaOCH_2CH_3$ or triethylamine in a solvent such as acetone, DMF, DMSO, acetonitrile, toluene, EtOH, and MeOH and optionally if appropriate a phase transfer catalyst such as tetrabutylammonium bromide or an additive such as a crown ether, tetrabutylammonium iodide or potassium iodide at room temperature 120° C. for 1-24 hours.

Preferred conditions are $K_2CO_3$ in DMF at 80° C. for 5 hours.

Step B:

The cleavage of the trityl group can be effected with a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C. Preferred conditions are 2N HCl in EtOH at reflux for 1-3 hours.

Procedure D

Synthesis of C—C-linked 2-methyl-4-imidazoles

Scheme 4

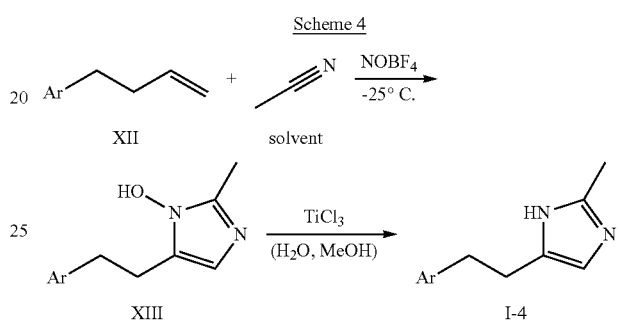

An appropriate olefin such as aryl-1-butene (XII) can be reacted at lower temperature with a nitrile such as acetonitrile and nitrosonium fluoroborate to form an imidazole-N-oxide according to Scheinbaum et al. (Tetrahedron Lett. 1971, p. 2205). To form the imidazole derivative 1-4 the hydroxyfunction can be removed by various reducing agents such as Red-Al, Titanium(III)-salts, Lithiumaluminiumhydride or others as described by Lipshutz et al. in Tetrahedron Lett. 25, 1984, p. 1319.

Procedure E

Synthesis of C—C-linked 2-amino-4-imidazoles

Scheme 5

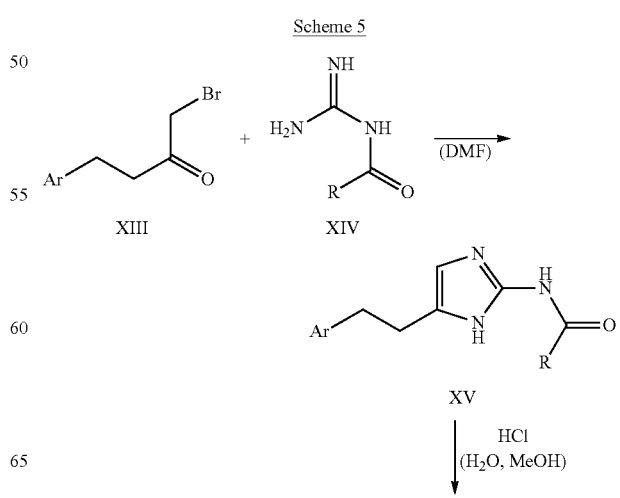

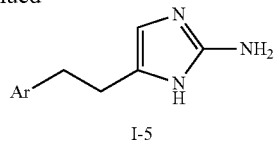

I-5

An alpha-bromoketone of formula XIII is reacted with an protected guanidine such as acetylguanidine (XIV) in a solvent such as dimethylformamide followed by deprotection of the amino group to form 2-aminoimidazole I-5. This deprotection can be achieved for instance by acid or base catalysed hydrolysis. In the case where the protecting group is an acetyl group, deprotection is preferably achieved by treatment with hydrochloric acid in a polar solvent such as water, alcohols or mixtures of water and alcohols.

Procedure F

Synthesis of C—S-Linked Compounds

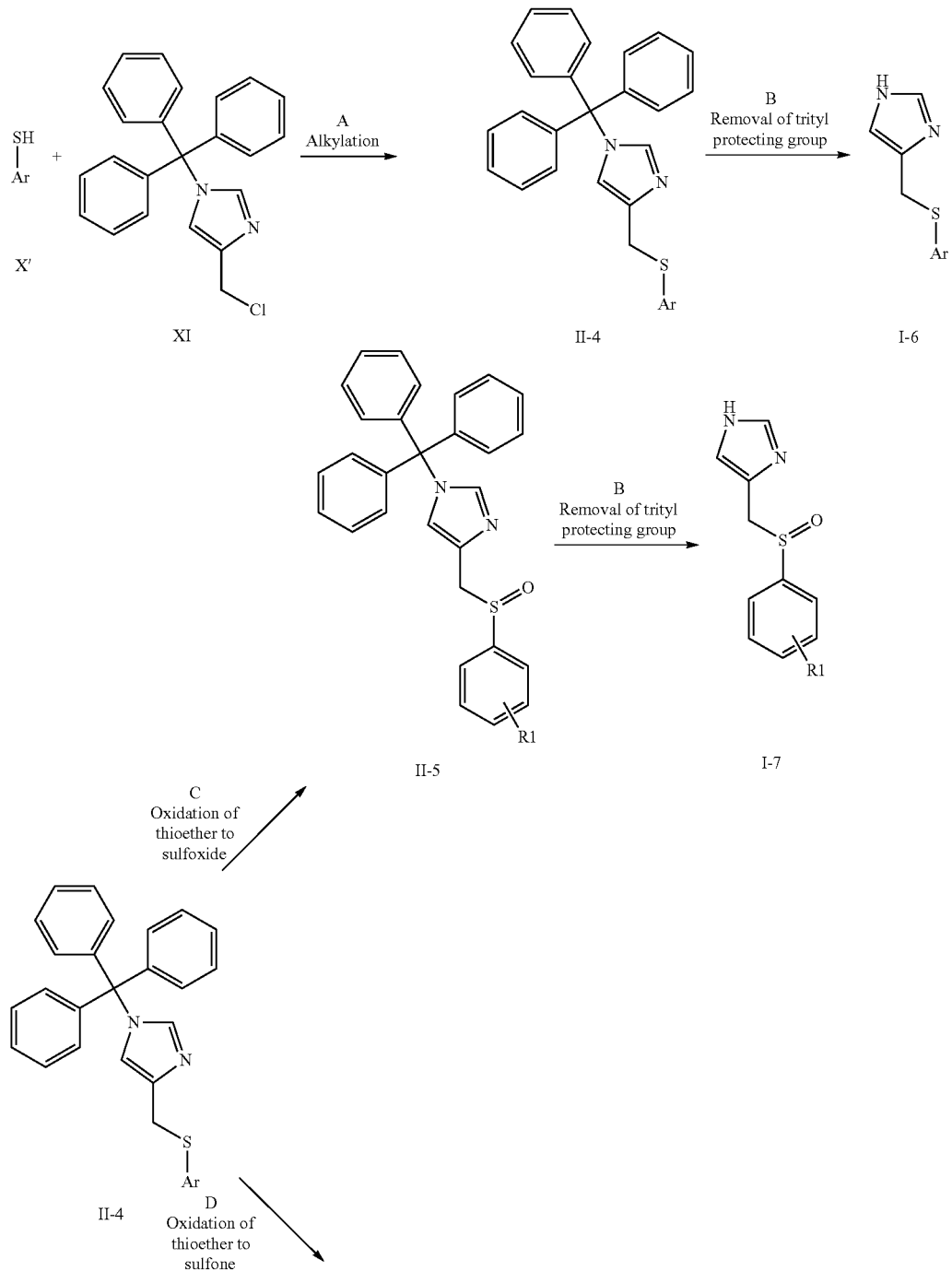

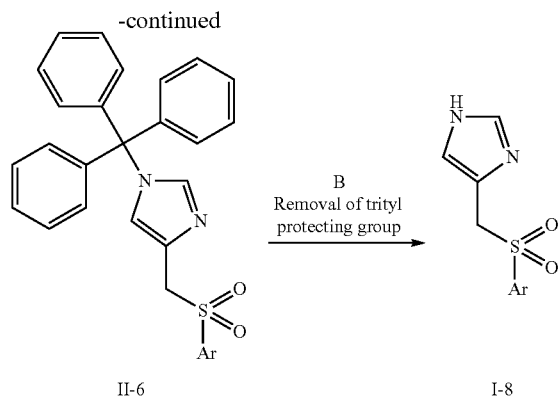

Step A:
The alkylation of a substituted phenol (X) with 4-chloromethyl-1-trityl-1H-imidazole (XI) can be accomplished using a base such as $K_2CO_3$, $Cs_2CO_3$, $Na_2CO_3$, $NaHCO_3$, aqueous NaOH, KOH, LiOH, NaH, $NaOCH_3$, $NaOCH_2CH_3$ or triethylamine in a solvent such as acetone, DMF, DMSO, acetonitrile, toluene, EtOH or MeOH and optionally if appropriate a phase transfer catalyst such as tetrabutylammonium bromide or an additive such as a crown ether, tetrabutylammonium iodide or potassium iodide at room temperature to 120° C. for 1-24 hours.

Preferred conditions are $K_2CO_3$ in DMF at 80° C. for 5 hrs.

Step B:
The cleavage of the trityl group can be effected with a mineral acid such as HCl, $H_2SO_4$ or $H_3PO_4$ or a organic acid such as $CF_3COOH$, $CHCl_2COOH$, HOAc or p-toluenesulfonic acid in a solvent such as $CH_2Cl_2$, $CHCl_3$, THF, MeOH, EtOH or $H_2O$ at 0 to 60° C. Preferred conditions are 2N HCl in EtOH at reflux for 1-3 hrs.

Step C:
The oxidation of the thioether (II-4) to the corresponding sulfoxide (II-5) can be accomplished by oxidants such as mCPBA, isopropyl 2-iodoxybenzoate, oxone or natriumperiodate in a solvent such as $CH_2Cl_2$, dichloroethane, toluene, acetonitrile, MeOH at temperatures from 0° C. to reflux.

Preferred conditions are 1 equivalent of mCPBA in $CH_2Cl_2$ at 0° C. to room temperature for 1-5 hours.

Step D:
The oxidation of the thioether (II-4) to the corresponding sulfoxide (II-6) can be accomplished by oxidants such as mCPBA, $H_2O_2$, oxone or sodium wolframate in a solvent such as $CH_2Cl_2$, dichloroethane, toluene, acetonitrile, THF, acetone, or MeOH at temperatures from 0° C. to reflux.

Preferred conditions are 2 equivalent of mCPBA in $CH_2Cl_2$ at 0° C. to room temperature for 1 to 5 hrs.

Procedure E

Synthesis of C—N-Linked Compounds

Scheme 7

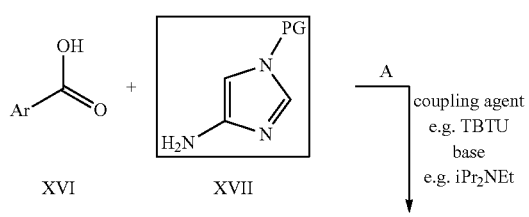

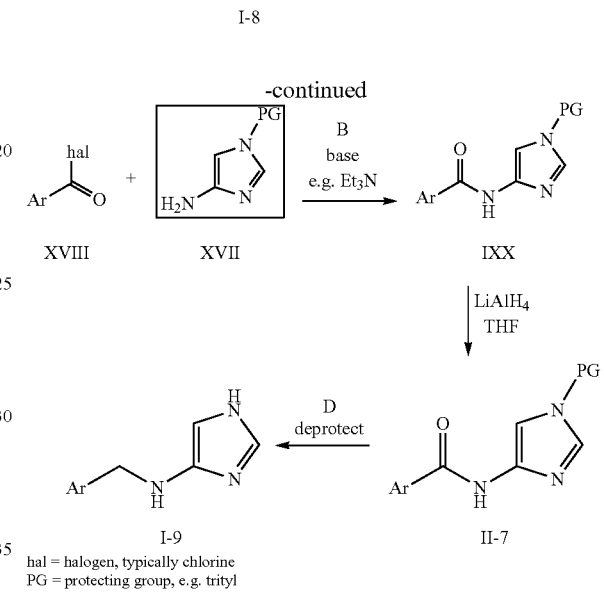

hal = halogen, typically chlorine
PG = protecting group, e.g. trityl

Step A:
The coupling of a substituted arylcarboxylic acid (XVI) with a suitably protected 4-amino-imidazole compound (XVII) to afford an amide compound (IXX) can be accomplished using a coupling agent such as 2-(1h-benzotriazole-1-yl)-1,1,3,3-tetramethyluronium tetrafluoroborate (TBTU) or 2-(1h-benzotriazole-1-yl)-1,1,3,3-tetramethyluronium hexafluorophosphate (HBTU) or o-(7-azabenzotriazol-1-yl)-n,n,n',n'-tetramethyluronium hexafluorophosphate (HATU) and a base such as triethylamine or ethyldiisopropylamine in a solvent such as THF, DMF, or dichloromethane. Suitable nitrogen protecting groups include tert-butoxycarbamate (BOC), trityl, dimethylaminosulfonyl and trimethylsilylethyl (SEM). Preferred conditions are TBTU and ethyldiisopropylamine in DMF at 40° C. for 16 hrs, and a preferred protecting group is trityl.

Step B:
The coupling of a substituted arylcarboxylic acid chloride (XVIII) with a suitably protected 4-amino-imidazole compound (XVII) to afford an amide compound (IXX) can be accomplished using a base such as pyridine, triethylamine or ethyldiisopropylamine in a solvent such as THF, DMF or dichloromethane and optionally using a catalyst such as N,N-dimethylformamide or 4-N,N-dimethylaminopyridine (DMAP)

Preferred conditions are triethylamine in dichloromethane at room temperature for 1 hour, and a preferred protecting group is trityl.

Step C:

The reduction of an amide (IXX) to an amine (II-7) can be accomplished using a metal hydride reducing agent such as lithium aluminium hydride or a borane reagent such as borane-tetrahydrofuran complex in a solvent such as dioxane, ether or tetrahydrofuran at elevated temperature.

Preferred conditions are lithium aluminium hydride in tetrahydrofuran at reflux temperature for 16 hours.

Step D:

The deprotection conditions depend on the nature of the protecting group employed and many methods are well known in the art.

In the case of the trityl protecting group, preferred deprotection conditions are 4 M aqueous hydrochloric acid in dioxane at room temperature for 1-2 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid-addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid-addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

Another aspect of the present invention is a pharmaceutical composition comprising a compound of formula I, or a pharmaceutically-suitable acid-addition salt thereof, and a therapeutically-inert carrier. Processes for the production of such a composition are also aspects of the present invention. Such a process comprises bringing one or more compounds of formula I and/or a pharmaceutically-suitable salt(s) thereof and, if desired, one or more other therapeutically-valuable substances into a galenical administration form together with one or more therapeutically-inert carriers.

The term "therapeutically-inert carrier" means that the carrier is not toxic and does not interfere with the ability of the active compound(s) to elicit the biological or medical response of a tissue system, animal or human that is being sought by the researcher, veterinarian, medical doctor or other clinician. The therapeutically-inert carrier for use in the composition of the present invention may be inorganic or organic. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. The composition can also contain still other therapeutically valuable substances.

The pharmaceutical composition of the present invention can be administered orally, e.g. in the form of tablets, coated tablets, dragées, hard and soft gelatine capsules, solutions, emulsions or suspensions. The administration can, however, also be effected rectally, e.g. in the form of suppositories, and parenterally, e.g. in the form of injection solutions.

The present invention relates also to a method for treating or preventing a disease or disorder in a patient comprising administering a therapeutically-effective amount of a compound of the present invention to a patient. A "therapeutically-effective amount" is the amount of the subject compound that will elicit the biological or medical response of a tissue system, animal or human that is being sought by the researcher, veterinarian, medical doctor or other clinician. The above method may involve the administration of a composition which comprises a therapeutically-effective amount of the compound such as the composition described above.

The therapeutically-effective amount can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically-suitable salt thereof. The daily dosage may be administered as single dose or in divided doses and, in addition, the upper limit can also be exceeded when this is found to be indicated.

EXAMPLES

The following examples illustrate the invention but are not intended to limit its scope.

Example 1

4-(2-Phenyl-butyl)-1H-imidazole a) 4-(2-Phenyl-but-1-enyl)-1-trityl-1H-imidazole

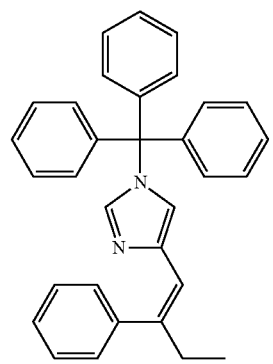 [SMILES: CC/C(=C/c1cn(C(c2ccccc2)(c2ccccc2)c2ccccc2)cn1)c1ccccc1]

To a stirred solution of (1-trityl-1H-imidazol-4-ylmethyl)-phosphonic acid diethyl ester (1.24 g; CAS 473659-21-1) at room temperature (r.t.) in THF (20 ml) under an argon atmosphere was added potassium tert-butylate (301 mg). After 15 minutes stirring at room temperature, propiophenone (0.3 ml) was added in one portion. The mixture was heated to 80° C. and stirring at that temperature was continued for 2 days. The compact suspension was cooled to r.t. and the solid was filtered off and washed with THF. The filtrate was concentrated to leave a dark violet viscous oil. This was taken up in ethyl acetate (EtOAc) and washed with brine. The aqueous phase was back extracted with EtOAc. The combined organics were washed with brine, dried over MgSO4, filtered and concentrated. The crude product was purified by column chromatography (silica gel; gradient cyclohexane→cyclohexane/EtOAc 3:2) to give 4-(2-phenyl-but-1-enyl)-1-trityl-1H-imidazole (269 mg; not completely pure) as an off-white solid. MS (ISP): 243.2 ([Trt]$^+$)

b) 4-(2-Phenyl-butyl)-1H-imidazole

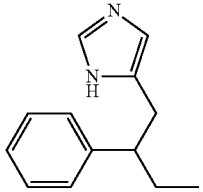

To a stirred solution of 4-(2-phenyl-but-1-enyl)-1-trityl-1H-imidazole (260 mg) at r.t. in methanol (5 ml) and dichloromethane (2 ml) under an argon atmosphere was added 10% Pd/C (26 mg). The mixture was then stirred at r.t. under a hydrogen atmosphere for 17 hours. The catalyst was filtered off and washed with methanol. The filtrate was concentrated. The crude product was purified by column chromatography (silica gel; gradient: $CH_2Cl_2$→$CH_2Cl_2$/MeOH 9:1 to give 4-(2-phenyl-butyl)-1H-imidazole (18 mg) as colorless gum. MS (ISP): 201.3 ([M+H]$^+$)

Example 2

4-(3-Methyl-2-phenyl-butyl)-1H-imidazole a) 4-(3-Methyl-2-phenyl-but-1-enyl)-1-trityl-1H-imidazole

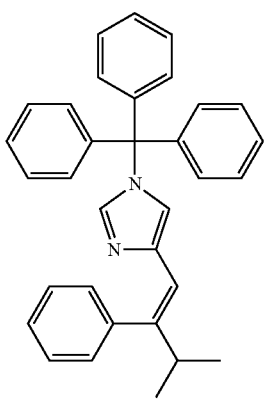 [SMILES: CC(C)/C(=C/c1cn(C(c2ccccc2)(c2ccccc2)c2ccccc2)cn1)c1ccccc1]

To a stirred suspension of (1-trityl-1H-imidazol-4-ylmethyl)-phosphonic acid diethyl ester (921 mg; CAS 473659-21-1) at r.t. in THF (20 ml) under an argon atmosphere was added potassium tert-butylate (241 mg). The mixture was then stirred at r.t. for 15 minutes, and isobutyrophenone (0.25 ml) was added in one portion. The mixture (clear brown orange solution) was heated to 80° C. for 21 hours. The reaction mixture was filtered and the cake was washed with EtOAc. The filtrate was concentrated. The crude product was purified by column chromatography (silica gel; gradient: cyclohexane→cyclohexane/EtOAc 1:1) to give 4-(3-methyl-2-phenyl-but-1-enyl)-1-trityl-1H-imidazole (91 mg; not completely pure) as orange sticky solid. MS (ISP): 243.2 ([Trt]$^+$)

b) 4-(3-Methyl-2-phenyl-butyl)-1-trityl-1H-imidazole

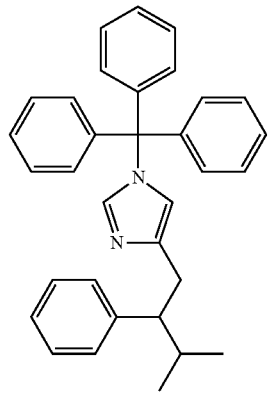 [SMILES: CC(C)C(Cc1cn(C(c2ccccc2)(c2ccccc2)c2ccccc2)cn1)c1ccccc1]

To a stirred solution of 4-(3-methyl-2-phenyl-but-1-enyl)-1-trityl-1H-imidazole (87 mg) at r.t. in methanol (4 ml) and $CH_2Cl_2$ (1 ml) under an argon atmosphere was added the 10% Pd/C (10 mg). The mixture was then stirred at r.t. under a hydrogen atmosphere for 38 hours. The catalyst was filtered off and washed with MeOH. The filtrate was concentrated to leave 4-(3-methyl-2-phenyl-butyl)-1-trityl-1H-imidazole (82 mg) of an off-white sticky solid which was used in the next step without further purification. MS (ISP): 243.2 ([Trt]$^+$)

c) 4-(3-Methyl-2-phenyl-butyl)-1H-imidazole

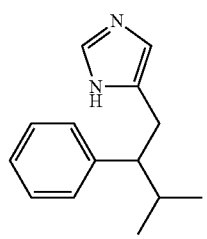 [SMILES: CC(C)C(Cc1cnc[nH]1)c1ccccc1]

To a stirred suspension of 4-(3-methyl-2-phenyl-butyl)-1-trityl-1H-imidazole (80 mg) at r.t. in ethanol (2 ml) under an argon atmosphere was added 2 N HCl (3 ml). The mixture (suspension) was heated to reflux (turning to a clear light yellow solution when reaching 90° C.) and stirred for 2 hours and 30 minutes, then cooled to r.t. and concentrated to leave a light brown sticky solid. This was taken up in $H_2O$ and basified to pH>12 by the addition of 4 N NaOH. The product was extracted with CH$_2$Cl$_2$/MeOH 9:1. The combined organics were dried over MgSO$_4$, filtered and concentrated. The crude product was purified by column chromatography (silica gel; gradient: CH$_2$Cl$_2$→CH$_2$Cl$_2$/MeOH 85:15) to give 4-(3-methyl-2-phenyl-butyl)-1H-imidazole (8 mg) as colorless gum. MS (ISP): 215.4 ([M+H]$^+$)

Example 3

4-(3,3-Dimethyl-2-phenyl-butyl)-1H-imidazole a) 4-(3,3-Dimethyl-2-phenyl-but-1-enyl)-1-trityl-1H-imidazole

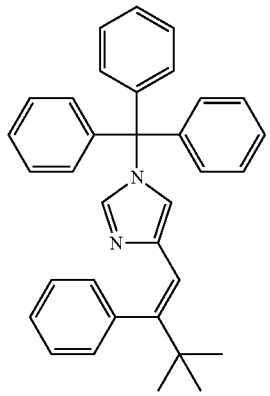 [SMILES: CC(C)(C)/C(=C/c1cn(C(c2ccccc2)(c2ccccc2)c2ccccc2)cn1)c1ccccc1]

To a stirred suspension of (1-trityl-1H-imidazol-4-ylmethyl)-phosphonic acid diethyl ester (341 mg; CAS 473659-21-1) at r.t. in THF (7.5 ml) under an argon atmosphere was added potassium tert-butylate (83 mg). The mixture was then stirred at r.t. for 15 minutes, and 2,2-dimethylpropiophenone (0.1 ml) was added in one portion. The mixture (clear brown orange solution) was heated to 80° C. and stirring at that temperature was continued for 24 hours. The reaction mixture was directly adsorbed on silica gel. The product was isolated by chromatography (gradient: cyclohexane→cyclohexane/EtOAc 65:35) to give 4-(3,3-dimethyl-2-phenyl-but-1-enyl)-1-trityl-1H-imidazole (135 mg; not completely pure) as light yellow solid. MS (ISP): 243.2 ([Trt]$^+$)

b) 4-(3,3-Dimethyl-2-phenyl-butyl)-1H-imidazole

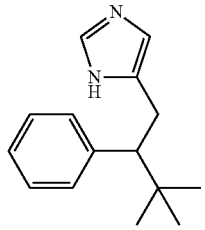 [SMILES: CC(C)(C)C(Cc1cnc[nH]1)c1ccccc1]

To a stirred solution of 4-(3,3-dimethyl-2-phenyl-but-1-enyl)-1-trityl-1H-imidazole (121 mg) at r.t. in methanol (5 ml) and dichloromethane (1 ml) under an argon atmosphere was added 10% Pd/C (12 mg). The mixture was stirred under a hydrogen atmosphere (balloon) for 17 hours. The catalyst was filtered off and washed with methanol. The filtrate was concentrated. The crude product was purified by column chromatography (silica gel; gradient: CH$_2$Cl$_2$→CH$_2$Cl$_2$/MeOH 9:1) to give 4-(3,3-dimethyl-2-phenyl-butyl)-1H-imidazole (25 mg) as colorless gum. MS (ISP): 229.4 ([M+H]$^+$)

Example 4

4-(1-Methoxy-2-phenyl-ethyl)-1H-imidazole a) 2-(tert-Butyl-dimethyl-silanyl)-4-formyl-imidazole-1-sulfonic acid dimethylamide

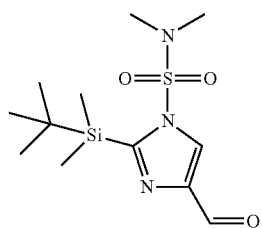 [SMILES: CN(C)S(=O)(=O)n1cc(C=O)nc1[Si](C)(C)C(C)(C)C]

To a stirred, cooled (−78° C.) solution of 2-(tert-butyl-dimethyl-silanyl)-imidazole-1-sulfonic acid dimethylamide (1.02 g; CAS 129378-52-5) in THF (20 ml) under an argon atmosphere was added dropwise butyl lithium (3.3 ml; 1.6 M solution in hexanes) over a period of 10 minutes. After 30 minutes of stirring, DMF (1.3 ml) was added over a period of 5 minutes and the mixture (clear light yellow solution) was stirred at −78° C. for another 2 hours. The mixture was quenched with saturated aqueous NH$_4$Cl and diluted with EtOAc. The aqueous phase was back extracted with EtOAc. The combined organics were washed with H$_2$O and brine, dried over MgSO$_4$, filtered and concentrated to give 2-(tert-butyl-dimethyl-silanyl)-4-formyl-imidazole-1-sulfonic acid dimethylamide (1.22 g) as viscous orange oil which was used in the next reaction step without further purification. MS (ISP): 318.3 ([M+H]$^+$)

b) 2-(tert-Butyl-dimethyl-silanyl)-4-(1-hydroxy-2-phenyl-ethyl)-imidazole-1-sulfonic acid dimethylamide

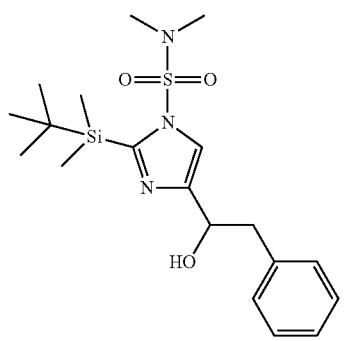 [SMILES: CN(C)S(=O)(=O)n1cc(C(O)Cc2ccccc2)nc1[Si](C)(C)C(C)(C)C]

Benzyl bromide (4.1 ml) was added dropwise to a stirred suspension of magnesium (1.01 g) in diethyl ether (10 ml). When the vigourously exothermic reaction was complete, the supernatant solution was decanted from the solid and kept in the fridge, ready for use. An aliquot of this solution (1 ml) was added dropwise (exothermic!) to a cooled (0° C., ice bath)

stirred solution of 2-(tert-butyl-dimethyl-silanyl)-4-formyl-imidazole-1-sulfonic acid dimethylamide (725 mg) at r.t. in THF (5 ml) under an argon atmosphere. When addition was complete, stirring at r.t. was continued overnight. The mixture was quenched by the addition of saturated aqueous NH$_4$Cl and extracted with EtOAc. The aqueous phase was back extracted with EtOAc. The combined organics were washed with H$_2$O and brine, dried over MgSO$_4$, filtered and concentrated. The crude product was purified by column chromatography (silica gel; gradient: cyclohexane→cyclohexane/EtOAc 25:75) to give 2-(tert-butyl-dimethyl-silanyl)-4-(1-hydroxy-2-phenyl-ethyl)-imidazole-1-sulfonic acid dimethylamide (168 mg) as light yellow solid. MS (ISP): 410.1 ([M+H]$^+$)

c) 2-(tert-Butyl-dimethyl-silanyl)-4-(1-methoxy-2-phenyl-ethyl)-imidazole-1-sulfonic acid dimethylamide

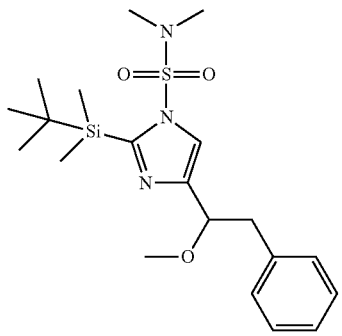 [SMILES: COC(Cc1ccccc1)c1cn(S(=O)(=O)N(C)C)c([Si](C)(C)C(C)(C)C)n1]

To a stirred solution of 2-(tert-butyl-dimethyl-silanyl)-4-(1-hydroxy-2-phenyl-ethyl)-imidazole-1-sulfonic acid dimethylamide (160 mg) at r.t. in THF (5 ml) under an argon atmosphere was added NaH (18 mg; 55% dispersion in mineral oil) in one portion. After 1 hour stirring at r.t., MeI (0.04 ml) was added and stirring at r.t. was continued overnight. The mixture was diluted with EtOAc and washed with H$_2$O. The aqueous phase was back extracted with EtOAc. The combined organics were washed with H$_2$O and brine, dried over MgSO$_4$, filtered and concentrated. The crude product was purified by column chromatography (silica gel; gradient: cyclohexane→cyclohexane/EtOAc 65:35) to give 2-(tert-butyl-dimethyl-silanyl)-4-(1-methoxy-2-phenyl-ethyl)-imidazole-1-sulfonic acid dimethylamide (111 mg) as light yellow viscous oil. MS (ISP): 424.3 ([M+H]$^+$)

d) 4-(1-Methoxy-2-phenyl-ethyl)-1H-imidazole

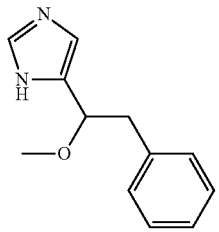

To a stirred suspension of 2-(tert-butyl-dimethyl-silanyl)-4-(1-methoxy-2-phenyl-ethyl)-imidazole-1-sulfonic acid dimethylamide (105 mg) at r.t. in ethanol (3 ml) under an argon atmosphere was added 2 N HCl (3 ml). The mixture was heated to reflux for 3 hours. The mixture was cooled to r.t. and concentrated to leave a light yellow solid which was taken up in H$_2$O and brought to pH 12 by the addition of 4 N NaOH. The product was extracted with CH$_2$Cl$_2$/MeOH 4:1. The combined organics were dried over MgSO4, filtered and concentrated. The crude product was purified by column chromatography (silica gel; gradient: CH$_2$Cl$_2$→CH$_2$Cl$_2$/MeOH 9:1) to give 4-(1-methoxy-2-phenyl-ethyl)-1H-imidazole (38 mg) as white solid. MS (ISP): 203.4 ([M+H]$^+$)

Example 5

4-[2-(2-Chloro-phenyl)-ethyl]-1H-imidazole a) 4-[2-(2-Chloro-phenyl)-vinyl]-1-trityl-1H-imidazole

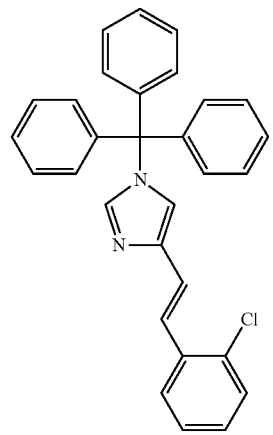 [SMILES: Clc1ccccc1/C=C/c1cn(C(c2ccccc2)(c2ccccc2)c2ccccc2)cn1]

To a stirred suspension of (1-trityl-1H-imidazol-4-ylmethyl)-phosphonic acid diethyl ester (448 mg; CAS 473659-21-1) at r.t. in THF (7 ml) under an argon atmosphere were added potassium tert-butylate (109 mg) and 2-chlorobenzaldehyde (114 mg). The mixture (clear brown orange solution) was heated to 80° C. over night. The reaction mixture was cooled to r.t and concentrated. The crude product was purified by column chromatography (silica gel; gradient: cyclohexane→cyclohexane/EtOAc 3:2) to give 4-[2-(2-chloro-phenyl)-vinyl]-1-trityl-1H-imidazole (329 mg) as off-white solid. MS (ISP): 243.3 ([Trt]$^+$)

b) 4-[2-(2-Chloro-phenyl)-ethyl]-1H-imidazole

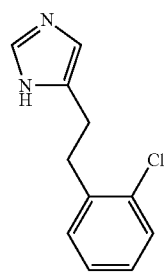 [SMILES: Clc1ccccc1CCc1cnc[nH]1]

To a stirred mixture of 4-[2-(2-chloro-phenyl)-vinyl]-1-trityl-1H-imidazole (329 mg) at r.t. in ethanol (7 ml) and chloroform (3 ml) under an argon atmosphere were added acetic acid (0.2 ml) and 10% Pd/C (30 mg). The mixture was hydrogenated (ambient pressure) over night. The catalyst was filtered off and washed with ethanol. The mixture was concentrated to leave a light brown gum. This material was taken up in ethanol (3 ml) and 2 N HCl (3 ml) and heated to reflux for 3 h. Then, the mixture was cooled to r.t., concentrated. The residual solid was taken up in 1 N NaOH (10 ml) and extracted with $CH_2Cl_2/MeOH$ 4:1. The combined organics were dried over $MgSO_4$, filtered and concentrated. The crude product was purified by column chromatography (silica gel; gradient: $CH_2Cl_2 \rightarrow CH_2Cl_2/MeOH$ 9:1) to give 4-[2-(2-chloro-phenyl)-ethyl]-1H-imidazole (44 mg) as light brown gum. MS (ISP): 207.1 ([M+H]$^+$)

Example 6

4-[2-(2-Ethyl-phenyl)-ethyl]-1H-imidazole

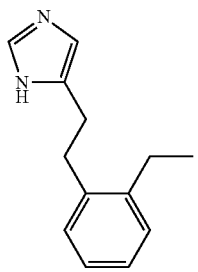

In analogy to example 5, (1-trityl-1H-imidazol-4-ylmethyl)-phosphonic acid diethyl ester (CAS 473659-21-1) was reacted with 2-ethylbenzaldehyde and then converted to 4-[2-(2-ethyl-phenyl)-ethyl]-1H-imidazole, as a colorless viscous oil. MS (ISP): 201.3 ([M+H]$^+$)

Example 7

4-[2-(2-Trifluoromethyl-phenyl)-ethyl]-1H-imidazole

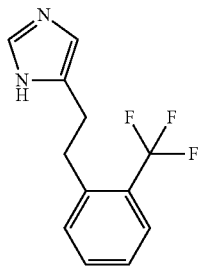 [SMILES: FC(F)(F)c1ccccc1CCc1cnc[nH]1]

In analogy to example 5, (1-trityl-1H-imidazol-4-ylmethyl)-phosphonic acid diethyl ester (CAS 473659-21-1) was reacted with 2-(trifluormethyl)benzaldehyde and then converted to 4-[2-(2-trifluoromethyl-phenyl)-ethyl]-1H-imidazole, as a colorless viscous oil. MS (ISP): 241.3 ([M+H]$^+$)

Example 8

4-[2-(2-Methoxy-phenyl)-ethyl]-1H-imidazole

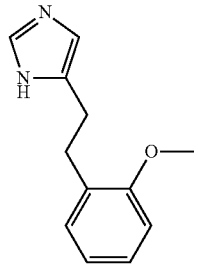

In analogy to example 5, (1-trityl-1H-imidazol-4-ylmethyl)-phosphonic acid diethyl ester (CAS 473659-21-1) was reacted with 2-methoxybenzaldehyde and then converted to 4-[2-(2-methoxy-phenyl)-ethyl]-1H-imidazole, as a colorless viscous oil. MS (ISP): 203.1 ([M+H]$^+$)

Example 9

{2-[2-(1H-Imidazol-4-yl)-ethyl]-phenyl}-dimethylamine

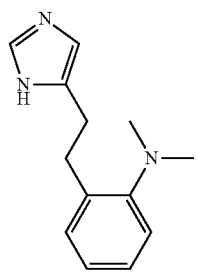 [SMILES: CN(C)c1ccccc1CCc1cnc[nH]1]

In analogy to example 5, (1-trityl-1H-imidazol-4-ylmethyl)-phosphonic acid diethyl ester (CAS 473659-21-1) was reacted with 2-(N,N-dimethylamino)benzaldehyde and then converted to {2-[2-(1H-Imidazol-4-yl)-ethyl]-phenyl}-dimethyl-amine, as a light yellow viscous oil. MS (ISP): 216.3 ([M+H]$^+$)

Example 10

4-{2-[2-(1H-Imidazol-4-yl)-ethyl]-phenyl}-morpholine

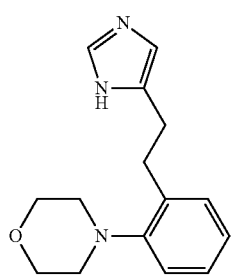 [SMILES: c1ccc(N2CCOCC2)c(CCc2cnc[nH]2)c1]

In analogy to example 5, (1-trityl-1H-imidazol-4-ylmethyl)-phosphonic acid diethyl ester (CAS 473659-21-1) was reacted with 2-morpholinobenzaldehyde and then converted to 4-{2-[2-(1H-imidazol-4-yl)-ethyl]-phenyl}-morpholine, as a light yellow viscous oil. MS (ISP): 258.3 ([M+H]$^+$)

Example 11

4-[2-(3-Chloro-phenyl)-ethyl]-1H-imidazole

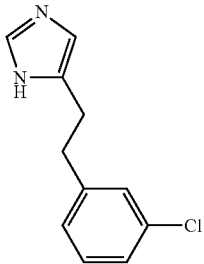 [SMILES: Clc1cccc(CCc2cnc[nH]2)c1]

In analogy to example 5, (1-trityl-1H-imidazol-4-ylmethyl)-phosphonic acid diethyl ester (CAS 473659-21-1) was reacted with 3-chlorobenzaldehyde and then converted to 4-[2-(3-chloro-phenyl)-ethyl]-1H-imidazole, as an off-white solid. MS (ISP): 207.1 ([M+H]$^+$)

Example 12

4-[2-(3-Fluoro-phenyl)-ethyl]-1H-imidazole

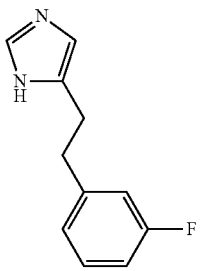 [SMILES: Fc1cccc(CCc2cnc[nH]2)c1]

In analogy to example 5, (1-trityl-1H-imidazol-4-ylmethyl)-phosphonic acid diethyl ester (CAS 473659-21-1) was reacted with 3-fluorobenzaldehyde and then converted to 4-[2-(3-fluoro-phenyl)-ethyl]-1H-imidazole, as an off-white solid. MS (ISP): 191.1 ([M+H]$^+$)

Example 13

4-[2-(3-Trifluoromethyl-phenyl)-ethyl]-1H-imidazole

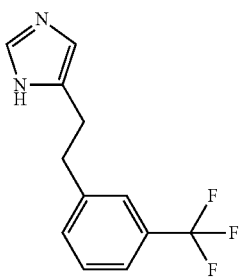 [SMILES: FC(F)(F)c1cccc(CCc2cnc[nH]2)c1]

In analogy to example 5, (1-trityl-1H-imidazol-4-ylmethyl)-phosphonic acid diethyl ester (CAS 473659-21-1) was reacted with 3-(trifluoromethyl)benzaldehyde and then converted to 4-[2-(3-trifluoromethyl-phenyl)-ethyl]-1H-imidazole, as an off-white viscous oil. MS (ISP): 241.1 ([M+H]$^+$)

Example 14

4-[2-(3-Methoxy-phenyl)-ethyl]-1H-imidazole

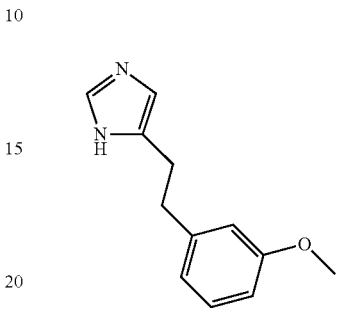

In analogy to example 5, (1-trityl-1H-imidazol-4-ylmethyl)-phosphonic acid diethyl ester (CAS 473659-21-1) was reacted with 3-methoxybenzaldehyde and then converted to 4-[2-(3-methoxy-phenyl)-ethyl]-1H-imidazole, as an off-white solid. MS (ISP): 203.3 ([M+H]$^+$)

Example 15

4-[2-(3-Trifluoromethoxy-phenyl)-ethyl]-1H-imidazole

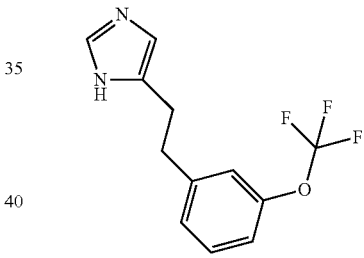

In analogy to example 5, (1-trityl-1H-imidazol-4-ylmethyl)-phosphonic acid diethyl ester (CAS 473659-21-1) was reacted with 3-(trifluoromethoxy)benzaldehyde and then converted to 4-[2-(3-trifluoromethoxy-phenyl)-ethyl]-1H-imidazole, as a light yellow viscous oil. MS (ISP): 257.3 ([M+H]$^+$)

Example 16

4-[2-(4-Chloro-phenyl)-ethyl]-1H-imidazole

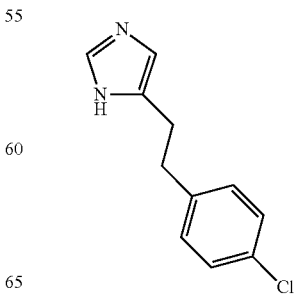

In analogy to example 5, (1-trityl-1H-imidazol-4-ylmethyl)-phosphonic acid diethyl ester (CAS 473659-21-1) was reacted with 4-chlorobenzaldehyde and then converted to 4-[2-(4-chloro-phenyl)-ethyl]-1H-imidazole, as an off-white solid. MS (ISP): 207.1 ([M+H]$^+$)

Example 17

4-[2-(3,5-Dichloro-phenyl)-ethyl]-1H-imidazole

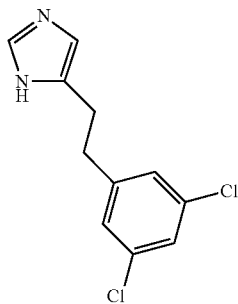 [SMILES: Clc1cc(Cl)cc(CCc2cnc[nH]2)c1]

In analogy to example 5, (1-trityl-1H-imidazol-4-ylmethyl)-phosphonic acid diethyl ester (CAS 473659-21-1) was reacted with 3,5-dichlorobenzaldehyde and then converted to 4-[2-(3,5-dichloro-phenyl)-ethyl]-1H-imidazole, as an off-white solid. MS (ISP): 241.1 ([M+H]$^+$)

Example 18

2-Methyl-5-phenethyl-1H-imidazole a) 2-Methyl-5-phenethyl-imidazol-1-ol

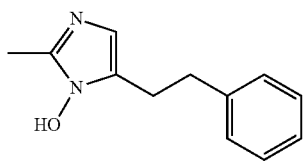

To a solution of nitrosonium tetrafluoroborate (0.564 g, 4.83 mmol) in acetonitrile (8 ml) 4-phenyl-1-butene was added at −30° C. The mixture was stirred for 1 hour at this temperature, then 0.5 ml of water was added carefully. At room temperature saturated ammonium chloride solution was added and the acetonitrile was evaporated in vacuo. The pH of the remaining aqueous solution was adjusted to neutral with a small amount of sodium hydroxide and extracted with dichloromethane. The organic layer was separated, dried over magnesium sulfate and evaporated. The residue was purified using flash chromatography (SiO$_2$, dichloromethane/methanol=9:1) to yield an off-white solid (0.245 g, 17%); MS (ISP): 202.9 ([M+H]$^+$)

b) 2-Methyl-5-phenethyl-1H-imidazole

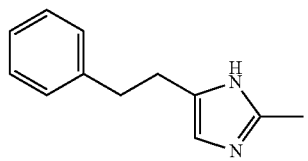

To a solution of 2-methyl-5-phenethyl-imidazol-1-ol (0.20 g, 1.0 mmol) in methanol (3.5 ml) titanium(III)-chloride solution (2.5 ml, 15%) was added and the mixture was stirred overnight at room temperature. First saturated sodium bicarbonate solution then diluted sodium hydroxide solution was added to achieve a basic pH. The mixture was extracted twice with dichloromethane, the combined organic layers were dried over magnesium sulfate and evaporated. The residue was purified by column chromatography (dichloromethane/methanol=9:1) to yield a white solid (0.14 mg, 75%); MS (EI): 186.1 (M$^+$).

Example 19

5-Phenethyl-1H-imidazol-2-ylamine

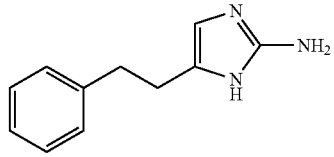 [SMILES: Nc1ncc(CCc2ccccc2)[nH]1]

To a solution of 1-acetylguanidine (1.34 g, 13.2 mmol) in dimethylformamide (7 ml) a solution of 1-bromo-4-phenyl-butan-2-one (1.5 g, 6.6 mmol) in dimethylformamide (7 ml) was added at 0° C. The mixture was stirred overnight at room temperature and then the solvent was evaporated. Upon addition of ethyl acetate/heptane (1:1) a white solid was formed that was filtered off and washed with ethyl acetate/heptane (1:1). After drying in vacuo the solid was dissolved in a mixture of concentrated hydrochloric acid (2 ml) and methanol (4 ml) and stirred for 2.5 hours at 85° C. The solvent was evaporated and the residue was purified by chromatography (column: Isolute Flash-NH$_2$ from Separtis; eluent: ethyl acetate/methanol=1:1) to yield a light yellow solid (0.063 mg, 5%); MS (EI): 187.2 (M$^+$).

Example 20

4-(2,3-Dichloro-phenoxymethyl)-1H-imidazole a) 4-(2,3-Dichloro-phenoxymethyl)-1-trityl-1H-imidazole

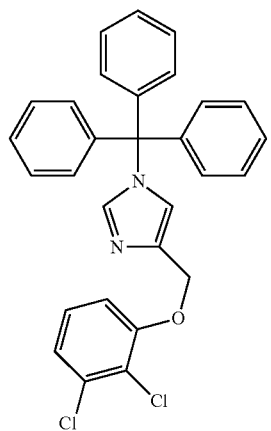 [SMILES: Clc1cccc(OCc2cn(C(c3ccccc3)(c3ccccc3)c3ccccc3)cn2)c1Cl]

To a stirred solution of 4-chloromethyl-1-trityl-1H-imidazole (400 mg; CAS 103057-10-9) at r.t. in DMF (5 ml) under an argon atmosphere were added 2,3-dichlorophenol (273 mg) and $K_2CO_3$ (385 mg). The reaction mixture was heated to 80° C. for 5 hours, then cooled to r.t., diluted with EtOAc and washed with 1 N NaOH. The aqueous phase was back extracted with EtOAc. The combined organics were washed with $H_2O$ and brine, dried over $MgSO_4$, filtered and concentrated. The crude product was purified by column chromatography (silica gel; gradient: cyclohexane→cyclohexane/ EtOAc 1:1) to give 4-(2,3-dichloro-phenoxymethyl)-1-trityl-1H-imidazole (360 mg) as white solid. MS (ISP): 243.3 ([Trt]$^+$)

b) 4-(2,3-Dichloro-phenoxymethyl)-1H-imidazole

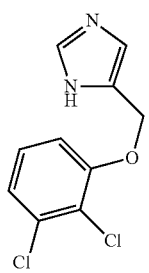 [SMILES: Clc1cccc(OCc2cnc[nH]2)c1Cl]

To a stirred suspension of 4-(2,3-dichloro-phenoxymethyl)-1-trityl-1H-imidazole (150 mg) at r.t. in ethanol (2 ml) under an argon atmosphere was added 2 N HCl (3 ml). The mixture was heated to reflux for 6 hours, then concentrated to leave an off-white solid. This was taken up in saturated aqueous $Na_2CO_3$ and extracted with $CH_2Cl_2$/MeOH 4:1. The combined organics were dried over $MgSO_4$, filtered and concentrated. The crude product was purified by column chromatography (silica gel; gradient: $CH_2Cl_2$→$CH_2Cl_2$/MeOH 4:1) to give 4-(2,3-dichloro-phenoxymethyl)-1H-imidazole (65 mg) as white solid. MS (ISP): 243.4 ([M+H]$^+$)

Example 21

4-(2-Ethyl-phenoxymethyl)-1H-imidazole

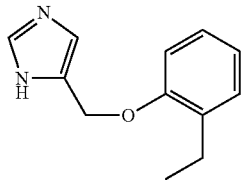

In analogy to example 20, 4-chloromethyl-1-trityl-1H-imidazole (CAS103057-10-9) was reacted with 2-ethylphenol and then converted to 4-(2-ethyl-phenoxymethyl)-1H-imidazole, as a waxy off-white solid. MS (ISP): 203.1 ([M+H]$^+$)

Example 22

4-(2-Isopropyl-phenoxymethyl)-1H-imidazole

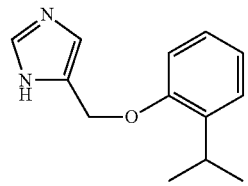 [SMILES: CC(C)c1ccccc1OCc1cnc[nH]1]

In analogy to example 20, 4-chloromethyl-1-trityl-1H-imidazole (CAS103057-10-9) was reacted with 2-isopropylphenol and then converted to 4-(2-isopropyl-phenoxymethyl)-1H-imidazole, as a waxy off-white solid. MS (ISP): 217.4 ([M+H]$^+$)

Example 23

4-(2-Trifluoromethyl-phenoxymethyl)-1H-imidazole

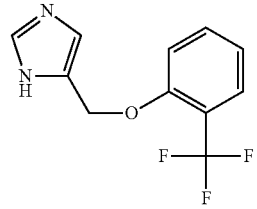 [SMILES: FC(F)(F)c1ccccc1OCc1cnc[nH]1]

In analogy to example 20, 4-chloromethyl-1-trityl-1H-imidazole (CAS103057-10-9) was reacted with 2-trifluoromethylphenol and then converted to 4-(2-trifluoromethyl-phenoxymethyl)-1H-imidazole, as a white solid. MS (ISP): 243.4 ([M+H]$^+$)

Example 24

4-(2-Benzyl-phenoxymethyl)-1H-imidazole

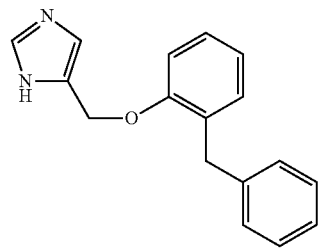 [SMILES: c1ccc(Cc2ccccc2OCc2cnc[nH]2)cc1]

In analogy to example 20, 4-chloromethyl-1-trityl-1H-imidazole (CAS103057-10-9) was reacted with 2-benzylphenol and then converted to 4-(2-benzyl-phenoxymethyl)-1H-imidazole, as a waxy white solid. MS (ISP): 265.1 ([M+H]⁺)

Example 25

4-(2-Methoxy-phenoxymethyl)-1H-imidazole

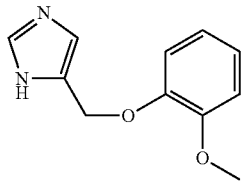

In analogy to example 20, 4-chloromethyl-1-trityl-1H-imidazole (CAS103057-10-9) was reacted with 2-methoxyphenol and then converted to 4-(2-methoxy-phenoxymethyl)-1H-imidazole as an off-white amorphous solid. MS (ISP): 205.1 ([M+H]⁺)

Example 26

4-(2-Isopropoxy-phenoxymethyl)-1H-imidazole

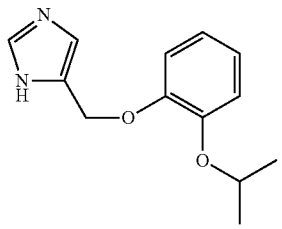 [SMILES: CC(C)Oc1ccccc1OCc1cnc[nH]1]

In analogy to example 20, 4-chloromethyl-1-trityl-1H-imidazole (CAS103057-10-9) was reacted with 2-isopropoxyphenol and then converted to 4-(2-isopropoxy-phenoxymethyl)-1H-imidazole as an off-white solid. MS (ISP): 233.3 ([M+H]⁺)

Example 27

4-(2-Trifluoromethoxy-phenoxymethyl)-1H-imidazole

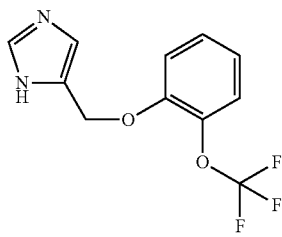 [SMILES: FC(F)(F)Oc1ccccc1OCc1cnc[nH]1]

In analogy to example 20, 4-chloromethyl-1-trityl-1H-imidazole (CAS103057-10-9) was reacted with 2-trifluoromethoxyphenol and then converted to 4-(2-trifluoromethoxy-phenoxymethyl)-1H-imidazole as an off-white solid. MS (ISP): 259.1 ([M+H]⁺)

Example 28

4-(2-Benzyloxy-phenoxymethyl)-1H-imidazole a) 4-(2-Benzyloxy-phenoxymethyl)-1-trityl-1H-imidazole

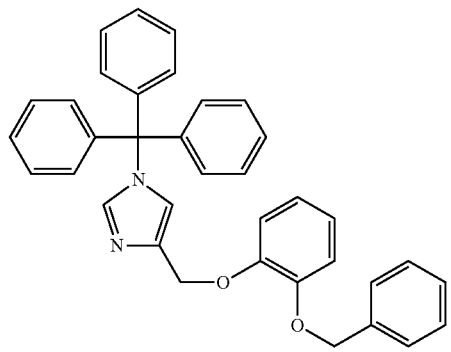 [SMILES: c1ccc(COc2ccccc2OCc2cn(C(c3ccccc3)(c3ccccc3)c3ccccc3)cn2)cc1]

In analogy to example 20.a., 4-chloromethyl-1-trityl-1H-imidazole (CAS103057-10-9) was reacted with 2-benzyloxyphenol to give 4-(2-benzyloxy-phenoxymethyl)-1-trityl-1H-imidazole as a yellow viscous oil. MS (ISP): 523.5 ([M+H]⁺)

b) 4-(2-Benzyloxy-phenoxymethyl)-1H-imidazole

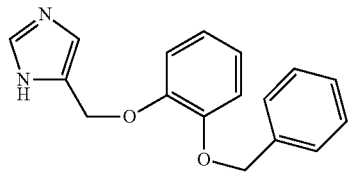 [SMILES: c1ccc(COc2ccccc2OCc2cnc[nH]2)cc1]

A solution of 4-(2-benzyloxy-phenoxymethyl)-1-trityl-1H-imidazole (34 mg) in MeOH (2 ml) was treated with AcOH (0.1 ml) and was heated to 70° C. for 5 hours. The mixture was concentrated. The crude product was purified by column chromatography to give 4-(2-benzyloxy-phenoxymethyl)-1H-imidazole (11 mg) as a colorless amorphous solid. MS (ISP): 281.4 ([M+H]⁺)

Example 29

2-(1H-Imidazol-4-ylmethoxy)-phenol

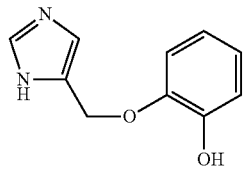 [SMILES: Oc1ccccc1OCc1cnc[nH]1]

Under conditions as described in example 20.b, 4-(2-benzyloxy-phenoxymethyl)-1-trityl-1H-imidazole (example 28.a) was converted to 2-(1H-Imidazol-4-ylmethoxy)-phenol as an off-white solid. MS (ISP): 191.4 ([M+H]$^+$)

Example 30

4-(3-Trifluoromethyl-phenoxymethyl)-1H-imidazole

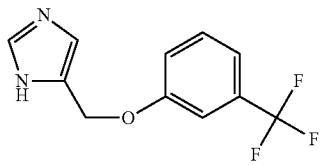 [SMILES: FC(F)(F)c1cccc(OCc2cnc[nH]2)c1]

In analogy to example 20, 4-chloromethyl-1-trityl-1H-imidazole (CAS103057-10-9) was reacted with 3-trifluoromethylphenol and then converted to 4-(3-trifluoromethyl-phenoxymethyl)-1H-imidazole as a white solid. MS (ISP): 243.3 ([M+H]$^+$)

Example 31

4-(3-Trifluoromethoxy-phenoxymethyl)-1H-imidazole

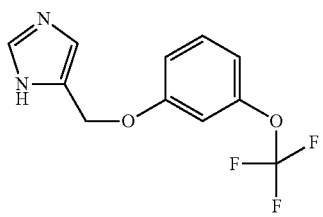 [SMILES: FC(F)(F)Oc1cccc(OCc2cnc[nH]2)c1]

In analogy to example 20, 4-chloromethyl-1-trityl-1H-imidazole (CAS103057-10-9) was reacted with 3-trifluoromethoxyphenol and then converted to 4-(3-trifluoromethoxy-phenoxymethyl)-1H-imidazole as a colorless oil. MS (ISP): 259.0 ([M+H]$^+$)

Example 32

[3-(1H-Imidazol-4-ylmethoxy)-phenyl]-dimethyl-amine

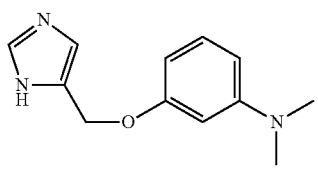 [SMILES: CN(C)c1cccc(OCc2cnc[nH]2)c1]

In analogy to example 20, 4-chloromethyl-1-trityl-1H-imidazole (CAS103057-10-9) was reacted with 3-dimethylaminophenol and then converted to [3-(1H-imidazol-4-ylmethoxy)-phenyl]-dimethyl-amine as an off-white solid. MS (ISP): 218.4 ([M+H]$^+$)

Example 33

4-[-(1H-Imidazol-4-ylmethoxy)-phenyl]-morpholine

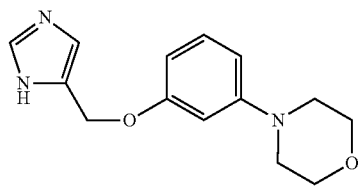 [SMILES: c1cc(OCc2cnc[nH]2)cc(N2CCOCC2)c1]

In analogy to example 20, 4-chloromethyl-1-trityl-1H-imidazole (CAS103057-10-9) was reacted with 3-morpholinophenol and converted to 4-[3-(1H-imdazol-4-ylmethoxy)-phenyl]-morpholine as a white solid. MS (ISP): 260.3 ([M+H]$^+$)

Example 34

4-(2,6-Diethyl-phenoxymethyl)-1H-imidazole

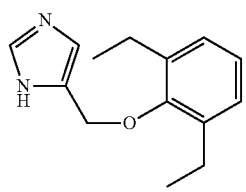 [SMILES: CCc1cccc(CC)c1OCc1cnc[nH]1]

In analogy to example 20, 4-chloromethyl-1-trityl-1H-imidazole (CAS103057-10-9) was reacted with 2,6-diethylphenol and converted to 4-(2,6-diethyl-phenoxymethyl)-1H-imidazole as a colorless oil. MS (ISP): 231.4 ([M+H]$^+$)

Example 35

4-(2,3-Difluoro-phenoxymethyl)-1H-imidazole

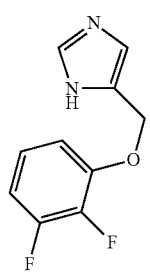 [SMILES: Fc1cccc(OCc2cnc[nH]2)c1F]

In analogy to example 20, 4-chloromethyl-1-trityl-1H-imidazole (CAS103057-10-9) was reacted with 2,3-difluorophenol and converted to 4-(2,3-difluoro-phenoxymethyl)-1H-imidazole as a white solid. MS (ISP): 211.1 ([M+H]⁺)

Example 36

4-(3,4-Dichloro-phenoxymethyl)-1H-imidazole

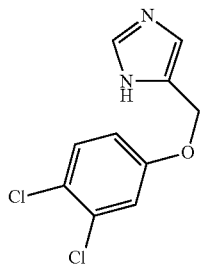 [SMILES: Clc1ccc(OCc2cnc[nH]2)cc1Cl]

In analogy to example 20, 4-chloromethyl-1-trityl-1H-imidazole (CAS103057-10-9) was reacted with 3,4-dichlorophenol and converted to 4-(3,4-dichloro-phenoxymethyl)-1H-imidazole as a white solid. MS (ISP): 243.1 ([M+H]⁺)

Example 37

4-(4-Chloro-3-fluoro-phenoxymethyl)-1H-imidazole

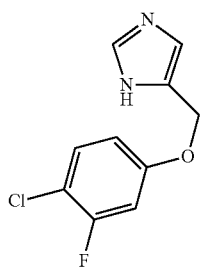 [SMILES: Fc1cc(OCc2cnc[nH]2)ccc1Cl]

In analogy to example 20, 4-chloromethyl-1-trityl-1H-imidazole (CAS103057-10-9) was reacted with 4-chloro-3-fluorophenol and converted to 4-(4-chloro-3-fluoro-phenoxymethyl)-1H-imidazole as a white solid. MS (ISP): 227.1 ([M+H]⁺)

Example 38

4-(3,4-Difluoro-phenoxymethyl)-1H-imidazole

In analogy to example 20, 4-chloromethyl-1-trityl-1H-imidazole (CAS103057-10-9) was reacted with 3,4-difluorophenol and converted to 4-(3,4-difluoro-phenoxymethyl)-1H-imidazole as a white solid. MS (ISP): 211.1 ([M+H]⁺)

Example 39

5-(Benzofuran-6-yloxymethyl)-1H-imidazole

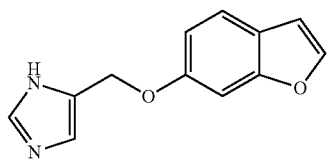 [SMILES: c1ncc(COc2ccc3ccoc3c2)[nH]1]

In analogy to example 20, 4-chloromethyl-1-trityl-1H-imidazole (CAS103057-10-9) was reacted with 6-hydroxybenzofurane and converted to 5-(benzofuran-6-yloxymethyl)-1H-imidazole.

Example 40

4-(3-Chloro-5-fluoro-phenoxymethyl)-1H-imidazole

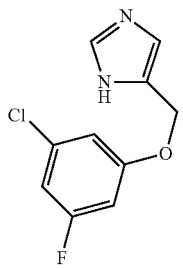 [SMILES: Fc1cc(Cl)cc(OCc2cnc[nH]2)c1]

In analogy to example 20, 4-chloromethyl-1-trityl-1H-imidazole (CAS103057-10-9) was reacted with 3-chloro-5-fluorophenol and converted to 4-(3-chloro-5-fluoro-phenoxymethyl)-1H-imidazole as an off-white amorphous solid. MS (ISP): 227.1 ([M+H]⁺)

Example 41

5-(4-Bromo-2,6-dimethyl-phenoxymethyl)-1H-imidazole

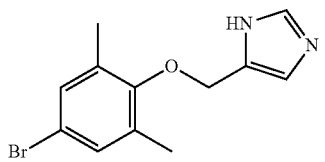 [SMILES: Cc1cc(Br)cc(C)c1OCc1cnc[nH]1]

In analogy to example 20, 4-chloromethyl-1-trityl-1H-imidazole (CAS103057-10-9) was reacted with 4-bromo-2,6-dimethylphenol and converted to 5-(4-bromo-2,6-dimethyl-phenoxymethyl)-1H-imidazole.

Example 42

5-(2,3-Dichloro-phenylsulfanylmethyl)-1-imidazole a) 5-(2,3-Dichloro-phenylsulfanylmethyl)-1-trityl-1-imidazole

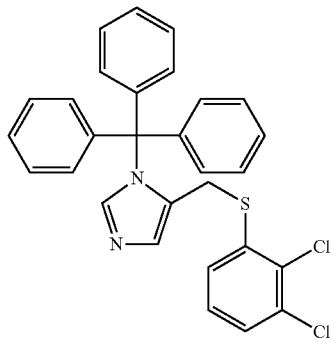 [SMILES: Clc1cccc(SCc2cncn2C(c2ccccc2)(c2ccccc2)c2ccccc2)c1Cl]

A solution of 4-chloromethyl-1-trityl-1H-imidazole (600 mg; CAS103057-10-9) in DMF (12 ml) was treated under an Argon atmosphere with potassium carbonate (578 mg) and 2,3-dichlorobenzenethiol (449 mg). The reaction mixture was heated to 80° C. for 5 hours, then cooled to r.t., taken up in water and extracted with EtOAc. The organic layer was washed with water, dried over MgSO4 and concentrated. The crude product was purified by column chromatography (silica gel; gradient: cyclohexane→cyclohexane/EtOAc 1:1) to give 5-(2,3-dichloro-phenylsulfanylmethyl)-1-trityl-1-imidazole (564 mg) as an off-white solid. MS (ISP): 243.3 ([Trt]$^+$)

b) 5-(2,3-Dichloro-phenylsulfanylmethyl)-1-imidazole

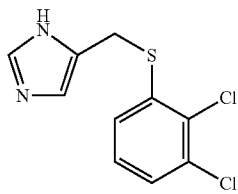 [SMILES: Clc1cccc(SCc2cnc[nH]2)c1Cl]

In analogy to example 20.b, 5-(2,3-dichloro-phenylsulfanylmethyl)-1-trityl-1-imidazole was converted to 5-(2,3-dichloro-phenylsulfanylmethyl)-1-imidazole as an off-white solid. MS (ISP): 259.0 ([M+H]$^+$)

Example 43

5-(2,3-Dichloro-benzenesulfinylmethyl)-1-imidazole a) 5-(2,3-Dichloro-benzenesulfinylmethyl)-1-trityl-1-imidazole

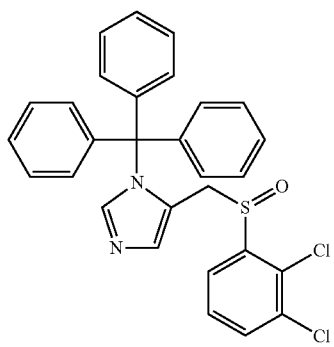 [SMILES: O=S(Cc1cncn1C(c1ccccc1)(c1ccccc1)c1ccccc1)c1cccc(Cl)c1Cl]

A solution of 5-(2,3-dichloro-phenylsulfanylmethyl)-1-trityl-1-imidazole (250 mg; example 42.a) in CH$_2$Cl$_2$ (20 ml) was cooled under an Argon atmosphere to 0° and treated with meta-chloroperbenzoic acid (86 mg). The reaction mixture was stirred for 3 hours at 0° C., then concentrated. The crude product was purified by column chromatography (silica gel; gradient: CH$_2$Cl$_2$→CH$_2$Cl$_2$/MeOH 98:2) to give 5-(2,3-dichloro-benzenesulfinylmethyl)-1-trityl-1-imidazole (121 mg) as a white solid. MS (ISP): 517.3 ([M+H]$^+$)

b) 5-(2,3-Dichloro-benzenesulfinylmethyl)-1-imidazole

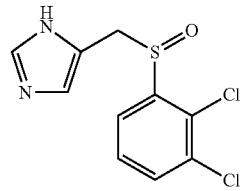 [SMILES: O=S(Cc1cnc[nH]1)c1cccc(Cl)c1Cl]

In analogy to example 20.b, 5-(2,3-dichloro-benzenesulfinylmethyl)-1-trityl-1-imidazole was converted to 5-(2,3-dichloro-benzenesulfinylmethyl)-1-imidazole as a white solid. MS (ISP): 275.1 ([M+H]$^+$)

Example 44

5-(2,3-Dichloro-benzenesulfonylmethyl)-1H-imidazole

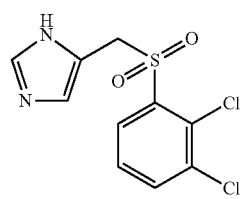 [SMILES: O=S(=O)(Cc1cnc[nH]1)c1cccc(Cl)c1Cl]

In analogy to example 43, but using 2 equivalents of meta-chloroperbenzoic acid in the first reaction step, 5-(2,3-dichloro-phenylsulfanylmethyl)-1-trityl-1-imidazole (250 mg; example 42.a) was converted to 5-(2,3-dichloro-benzenesulfonylmethyl)-1H-imidazole as a white solid. MS (ISP): 291.0 ([M+H]$^+$)

Example 45

4-Benzenesulfinylmethyl-5-methyl-1H-imidazole

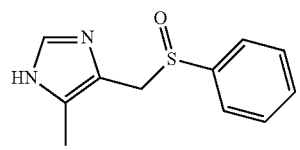

The title compound was prepared in analogy to example 43 using 4-chloromethyl-5-methyl-1-trityl-1H-imidazole (CAS106147-85-7) for the alkylation of benzenethiol.

Example 46

4-(4-Chloro-phenylsulfanylmethyl)-5-methyl-1H-imidazole

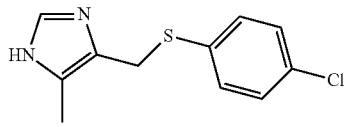

The title compound was prepared in analogy to example 42 using 4-chloromethyl-5-methyl-1-trityl-1H-imidazole (CAS106147-85-7) for the alkylation of 4-chlorobenzenethiol.

Example 47

4-(Naphthalen-2-ylsulfanylmethyl)-1H-imidazole

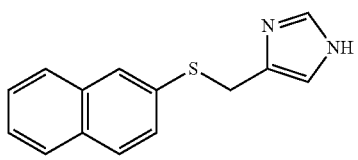 [SMILES: c1ccc2cc(SCc3c[nH]cn3)ccc2c1]

The title compound was prepared in analogy to example 42 starting from naphthalene-2-thiol.

Example 48

Benzyl-(1H-imidazol-4-yl)-amine hydrochloride a) N-(1-Trityl-1H-imidazol-4-yl)-benzamide

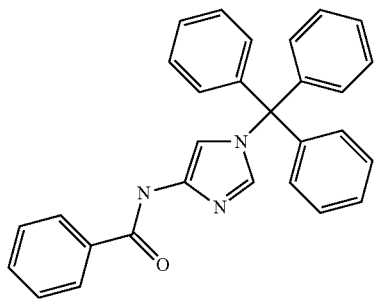 [SMILES: O=C(Nc1cn(C(c2ccccc2)(c2ccccc2)c2ccccc2)cn1)c1ccccc1]

To a solution of 4-amino-1-tritylimidazole (0.30 g, 0.92 mmol) in dichloromethane (4 ml) were added sequentially triethylamine (0.19 ml, 1.37 mmol) and benzoyl chloride (0.13 ml, 1.12 mmol). The reaction mixture was stirred at room temperature for 30 minutes, then diluted with dichloromethane and washed sequentially with water, saturated aq. NaHCO$_3$ solution, water and saturated brine. The organic layer was separated, dried over sodium sulfate and concentrated in vacuo. The residue was purified by chromatography on silica gel (eluant: methanol/dichloromethane 0:100 to 10:90) to yield the title compound as an orange solid (0.36 g, 92%); MS (ISP): 430.3 ([M+H]$^+$).

b) Benzyl-(1-trityl-1H-imidazol-4-yl)-amine

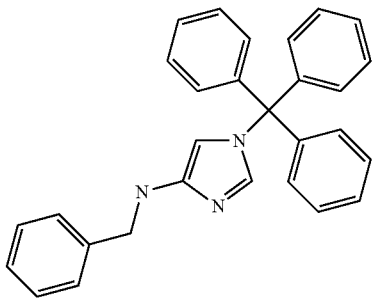 [SMILES: c1ccc(CNc2cn(C(c3ccccc3)(c3ccccc3)c3ccccc3)cn2)cc1]

To a solution of N-(1-trityl-1H-imidazol-4-yl)-benzamide (0.36 g, 0.83 mmol) in tetrahydrofuran (10 ml) was added portionwise lithium aluminium hydride (0.16 g, 4.14 mmol). The reaction mixture was stirred at 80° C. for 16 hours, then cooled to room temperature and water added dropwise. The mixture was stirred at room temperature for 20 minutes and then extracted with ethyl acetate. The organic layer was separated, washed with water, dried over magnesium sulfate and concentrated in vacuo. The residue was purified by chromatography on silica gel (eluant: methanol/dichloromethane 0:100 to 10:90) to yield the title compound as a white solid (0.15 g, 44%); MS (ISP): 416.5 ([M+H]$^+$).

c) Benzyl-(1H-imidazol-4-yl)-amine hydrochloride

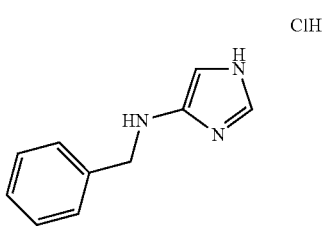 [SMILES: Cl ; c1ccc(CNc2c[nH]cn2)cc1]

Benzyl-(1-trityl-1H-imidazol-4-yl)-amine (0.15 g, 0.35 mmol) was dissolved in a 4 M solution of HCl in dioxane (5 ml). The mixture was stirred at room temperature for 90 minutes and then concentrated in vacuo. The residue was triturated in ether to yield the title compound as an off-white solid (73 mg, 100%); MS (ISP): 174.4 ([M+H]$^+$).

Compounds of examples 1-48 are new. Compounds of examples A-N are known.

Example 49

The ability of the compounds of the present invention to bind to TAAR1 was demonstrated in accordance with the test given hereinafter.

Materials and Methods

Construction of TAAR Expression Plasmids and Stably Transfected Cell Lines

For the construction of expression plasmids, the coding sequences of human, rat and mouse TAAR 1 were amplified from genomic DNA essentially as described by Lindemann et al. (2005) *Genomics* 85, 372-385. The Expand High Fidelity PCR System (Roche Diagnostics) was used with 1.5 mM $Mg^2F$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described in Lindemann et al. (2005) *Genomics* 85, 372-385. For the generation of stably transfected cell lines, HEK293 cells were transfected with the pIRESneo2 expression plasmids containing the TAAR coding sequences (described above) with Lipofectamine 2000 (Invitrogen) according to the instructions of the manufacturer, and 24 hours post transfection, the culture medium was supplemented with 1 mg/ml G418 (Sigma, Buchs, Switzerland). After a culture period of about 10 days, clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 minutes at 4° C. The pellet was then washed twice with ice-cold phosphate buffered saline and the cell pellet was frozen immediately by immersion in liquid nitrogen and stored until use at −80° C. The cell pellet was then suspended in 20 ml HEPES-NaOH (20 mM), pH 7.4 containing 10 mM EDTA, and homogenized with a Polytron (PT 3000, Kinematica) at 10,000 rpm for 10 seconds. The homogenate was centrifuged at 48,000×g for 30 minutes at 4° C. and the pellet resuspended in 20 ml HEPES-NaOH (20 mM), pH 7.4 containing 0.1 mM EDTA (buffer A), and homogenized with a Polytron at 10,000 rpm for 10 seconds. The homogenate was then centrifuged at 48,000×g for 30 minutes at 4° C. and the pellet resuspended in 20 ml buffer A, and homogenized with a Polytron at 10,000 rpm for 10 seconds. Protein concentration was determined by the method of Pierce (Rockford, Ill.). The homogenate was then centrifuged at 48,000×g for 10 minutes at 4° C., resuspended in HEPES-NaOH (20 mM), pH 7.0 including $MgCl_2$ (10 mM) and $CaCl_2$ (2 ml) (buffer B) at 200 µg protein per ml and homogenized with a Polytron at 10,000 rpm for 10 seconds.

Binding assay was performed at 4° C. in a final volume of 1 ml, and with an incubation time of 30 minutes. The radioligand [$^3$H]-rac-2-(1,2,3,4-tetrahydro-1-naphthyl)-2-imidazoline was used at a concentration equal to the calculated $K_d$ value of 60 nM to give a total binding at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 µM). Competing ligands were tested in a wide range of concentrations (10 µM-30 µM). The final dimethylsulphoxide concentration in the assay was 2%, and it did not affect radioligand binding. Each experiment was performed in duplicate. All incubations were terminated by rapid filtration through Uni-Filter-96 plates (Packard Instrument Company) and glass filter GF/C, pre-soaked for at least 2 hours in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 µl/well, Packard Instrument Company) and bound radioactivity was counted by a TopCount Microplate Scintillation Counter (Packard Instrument Company).

The preferred compounds show a Ki value (µM) in mouse on TAAR1 in the range of <0.1 µM as shown in the table below.

| Example | Ki (µM) mouse |
|---|---|
| 1 | 0.0609 |
| 5 | 0.0059 |
| 8 | 0.0843 |
| 11 | 0.0025 |
| 12 | 0.0097 |
| 13 | 0.0106 |
| 14 | 0.0606 |
| 16 | 0.0172 |
| 17 | 0.0019 |
| 20 | 0.043 |
| 35 | 0.0889 |
| 36 | 0.0227 |
| 37 | 0.0802 |
|  | Ki |
| 39 | 0.0684 |
| 42 | 0.0041 |
| 46 | 0.0146 |
| 47 | 0.0103 |

Example 50

Tablet Formulation (Wet Granulation)

| Item | Ingredients | 5 mg | 25 mg | 100 mg | 500 mg |
|---|---|---|---|---|---|
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
|  | Total | 167 | 167 | 167 | 831 |

Manufacturing Procedure

1. Mix items 1, 2, 3 and 4 and granulate with purified water.

2. Dry the granules at 50° C.

3. Pass the granules through suitable milling equipment.

4. Add item 5 and mix for three minutes; compress on a suitable press.

Example 52

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:

1. A compound according to formula I,

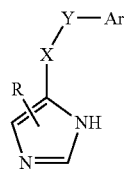

I wherein
R is selected from the group consisting of hydrogen, lower alkyl and amino;
X and Y are both —$CH_2$—; and
Ar is selected from the group consisting of phenyl, napthtyl and benzofuranyl, said phenyl, mapthyl, or benzofuranyl being unsubstituted or substituted by one or more substituents, each substituent being independently selected from the group consisting of lower alkyl, lower alkyl substituted by halogen, halogen, lower alkoxy, lower alkoxy substituted by halogen, hydroxy, amino, di-alkylamino, morpholinyl, phenyl, benzyl and O-benzyl;
or a pharmaceutically-suitable acid-addition salt thereof;
with the provisio that said compound is selected from the group consisting of:
4-[2-(2-chloro-phenyl)-ethyl]-1H-imidazole;
4-[2-(2-methoxy-phenyl)-ethyl]-1H-imidazole;
4-[2-(3-chloro-phenyl)-ethyl]-1H-imidazole;
4-[2-(3-fluoro-phenyl)-ethyl]-1H-imidazole;
4-[2-(3-trifluoromethyl-phenyl)-ethyl]-1H-imidazole;
4-[2-(3-methoxy-phenyl)-ethyl]-1H-imidazole;
4-[2-(4-chloro-phenyl)-ethyl]-1H-imidazole;
4-[2-(3,5-dichloro-phenyl)-ethyl]-1H-imidazole;
4-[2-(2-ethyl-phenyl)-ethyl]-1H-imidazole;
4-[2-(2-trifluoromethyl-phenyl)-ethyl]-1H-imidazole;
{2-[2-(1H-imidazol-4-yl)-ethyl]-phenyl}-dimethylamine;
4-{2-[2-(1H-imidazol-4-yl)-ethyl]-phenyl}-morpholine;
4-[2-(3-trifluoromethoxy-phenyl)-ethyl]-1H-imidazole;
2-methyl-5-phenethyl-1H-imidazole;
5-phenethyl-1H-imidazol-2-ylamine; and
pharmaceutically-suitable acid-addition salts thereof.

2. A compound according to claim 1, selected from the group consisting of:
4-[2-(2-chloro-phenyl)-ethyl]-1H-imidazole;
4-[2-(2-methoxy-phenyl)-ethyl]-1H-imidazole;
4-[2-(3-chloro-phenyl)-ethyl]-1H-imidazole;
4-[2-(3-fluoro-phenyl)-ethyl]-1H-imidazole;
4-[2-(3-trifluoromethyl-phenyl)-ethyl]-1H-imidazole;
4-[2-(3-methoxy-phenyl)-ethyl]-1H-imidazole;
4-[2-(4-chloro-phenyl)-ethyl]-1H-imidazole;
4-[2-(3,5-dichloro-phenyl)-ethyl]-1H-imidazole; and
pharmaceutically-suitable acid-addition salts thereof.

3. A composition comprising a compound according to claim 1 and a therapeutically-inert carrier.

4. A process for the preparation of a compound according to claim 1, comprising deprotecting a compound according to formula II,

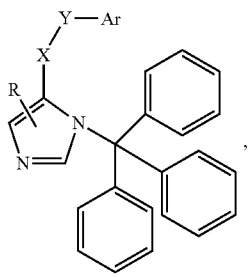

II wherein R, X, Y, and Ar have the same values as they have in formula I.

5. A compound according to claim 1 wherein said compound is selected from the group consisting of:
4-[2-(2-ethyl-phenyl)-ethyl]-1H-imidazole;
4-[2-(2-trifluoromethyl-phenyl)-ethyl]-1H-imidazole;
{2-[2-(1H-imidazol-4-yl)-ethyl]-phenyl}-dimethylamine;
4-{2-[2-(1H-imidazol-4-yl)-ethyl]-phenyl}-morpholine;
4-[2-(3-trifluoromethoxy-phenyl)-ethyl]-1H-imidazole;
2-methyl-5-phenethyl-1H-imidazole;
5-phenethyl-1H-imidazol-2-ylamine; and
pharmaceutically-suitable acid-addition salts thereof.

* * * * *